(12) United States Patent
Yoshihiko et al.

(10) Patent No.: US 11,330,990 B2
(45) Date of Patent: May 17, 2022

(54) BLOOD FLOW METER AND MEASUREMENT DEVICE

(71) Applicant: Nipro Corporation, Osaka (JP)

(72) Inventors: Sano Yoshihiko, Osaka (JP); Harada Masahide, Hokkaido (JP); Miyagawa Katsuya, Osaka (JP); Shimazaki Natsumi, Osaka (JP)

(73) Assignees: NIPRO CORPORATION; Harada Electronic Industry Ltd.

( * ) Notice: Subject to any disclaimer, the term of this patent is extended or adjusted under 35 U.S.C. 154(b) by 340 days.

(21) Appl. No.: 15/539,901

(22) PCT Filed: Jan. 4, 2016

(86) PCT No.: PCT/JP2016/050029
§ 371 (c)(1),
(2) Date: Jun. 26, 2017

(87) PCT Pub. No.: WO2016/111261
PCT Pub. Date: Jul. 14, 2016

(65) Prior Publication Data
US 2018/0263508 A1 Sep. 20, 2018

(30) Foreign Application Priority Data

Jan. 5, 2015 (JP) .............................. JP2015-000474

(51) Int. Cl.
*A61B 5/02* (2006.01)
*A61B 5/0215* (2006.01)
(Continued)

(52) U.S. Cl.
CPC ............ *A61B 5/0215* (2013.01); *A61B 5/028* (2013.01); *A61B 8/06* (2013.01); *G01L 19/0092* (2013.01); *A61B 5/02108* (2013.01)

(58) Field of Classification Search
CPC ....... A61B 8/06; A61B 5/028; A61B 5/02108; A61M 2025/0002
See application file for complete search history.

(56) References Cited

U.S. PATENT DOCUMENTS 3,452,742 A * 7/1969 Muller .............. A61M 25/0136
600/585
3,726,269 A * 4/1973 Webster, Jr. ........... A61B 5/028
600/526
(Continued)

FOREIGN PATENT DOCUMENTS

FR 2311309 A1 12/1976
JP 03-504041 A 9/1991
(Continued)

OTHER PUBLICATIONS

Chiguma, J., Johnson, E., Shah, P., Gornopolskaya, N., & Jones Jr, W. E. (2013). Thermal diffusivity and thermal conductivity of epoxy-based nanocomposites by the laser flash and differential scanning calorimetry techniques. Open Journal of Composite Materials, 3(03), 51. (Year: 2013).*
(Continued)

*Primary Examiner* — Majan Fardanesh
(74) *Attorney, Agent, or Firm* — Jordan and Koda, PLLC

(57) ABSTRACT

A blood flow meter capable of measuring the flow rate of the blood flow with high accuracy in a blood vessel of a living body is provided. An element holding body having a tubular shape and having an outer diameter smaller than or equal to the outer diameter of a hollow shaft, which has flexibility and is insertable into a blood vessel, is provided on the distal side of the shaft so as to be coaxial with the shaft. A flow rate sensor is accommodated in the element holding body. The flow rate sensor has a measurement element in which a nickel wire is spirally wound to be formed into a coil shape so that adjacent nickel wires are not in contact with each
(Continued)

other and are insulated. A thermal conductive insulating member is provided between the flow rate sensor and the element holding body in the element holding body and the flow rate sensor is fixed in the element holding body by the insulating member.

15 Claims, 17 Drawing Sheets

(51) Int. Cl.
*A61B 5/028* (2006.01)
*A61B 8/06* (2006.01)
*G01L 19/00* (2006.01)
*A61B 5/021* (2006.01)

(56) References Cited

U.S. PATENT DOCUMENTS

| | | | | |
|---|---|---|---|---|
| 4,240,441 A * | 12/1980 | Khalil | ............... | A61B 5/028 600/505 |
| 4,900,381 A * | 2/1990 | Guenther | ............ | A61B 5/14539 156/155 |
| 5,119,674 A * | 6/1992 | Nielsen | ............... | A61B 5/028 73/204.17 |
| 5,339,816 A * | 8/1994 | Akamatsu | ............... | A61B 5/028 600/455 |
| 5,373,850 A * | 12/1994 | Kohno | ............... | A61B 5/028 600/505 |
| 5,467,384 A * | 11/1995 | Skinner, Sr. | ............... | H04B 10/808 455/402 |
| 5,493,100 A * | 2/1996 | Renger | ............... | A61B 5/028 219/497 |
| 5,509,424 A * | 4/1996 | Al-Ali | ............... | A61B 5/028 128/925 |
| 5,617,870 A * | 4/1997 | Hastings | ............... | A61B 5/028 600/505 |
| 5,617,871 A * | 4/1997 | Burrows | ............... | A61B 5/0002 128/903 |
| 5,682,899 A * | 11/1997 | Nashef | ............... | A61B 5/028 600/505 |
| 5,873,835 A * | 2/1999 | Hastings | ............... | G01F 1/698 600/488 |
| 6,343,514 B1 * | 2/2002 | Smith | ............... | A61B 5/0215 374/E1.008 |
| 7,254,946 B1 * | 8/2007 | Quinn | ............... | A61B 18/14 60/505 |
| 2002/0043113 A1 * | 4/2002 | Tulkki | ............... | A61B 5/028 73/861.95 |
| 2004/0030266 A1 * | 2/2004 | Murayama | ............ | B21F 15/08 600/585 |
| 2005/0171446 A1 * | 8/2005 | Krivitski | ............... | A61B 17/22 600/504 |
| 2007/0167866 A1 * | 7/2007 | Lopez | ............... | A61B 5/028 600/549 |
| 2009/0163780 A1 * | 6/2009 | Tieu | ............... | A61B 17/12109 600/301 |
| 2011/0301686 A1 * | 12/2011 | Bowman | ............ | A61M 25/0021 623/1.11 |
| 2012/0071783 A1 * | 3/2012 | Klee | ............... | A61B 5/02007 600/549 |
| 2012/0172703 A1 * | 7/2012 | Esguerra | ............... | A61B 5/062 600/409 |
| 2013/0184705 A1 * | 7/2013 | Gelbart | ............... | A61B 18/1492 606/41 |
| 2014/0058277 A1 * | 2/2014 | Tan | ............... | A61B 5/6853 600/487 |
| 2018/0368702 A1 * | 12/2018 | Sette | ............... | G01F 1/69 |

FOREIGN PATENT DOCUMENTS

| | | |
|---|---|---|
| JP | 7-313475 | 12/1995 |
| JP | 11-244248 | 9/1999 |
| JP | 2000-504249 | 4/2000 |
| JP | 3696682 B2 | 9/2005 |

OTHER PUBLICATIONS

Bernland, Karin. "Hydrophobic epoxy resin for outdoor electrical insulation." (2005). (Year: 2005).*

* cited by examiner

BLOOD FLOW METER AND MEASUREMENT DEVICE

TECHNICAL FIELD

The present invention relates to a blood flow meter which is inserted into a blood vessel of a living body to acquire information on the blood flow and a measurement device employing the blood flow meter.

BACKGROUND ART

As one of the indices for determining the treatment policy of the stenosis lesion in the coronary artery, coronary flow reserve (CFR) is mentioned. The CFR is the index indicating the capability of increasing the coronary blood flow rate according to an increase in myocardial oxygen consumption and is determined based on the ratio of the coronary blood flow rate at the maximum hyperemia to the coronary blood flow rate at rest. A reduction in the CFR is considered to be the onset mechanism of myocardial ischemia in view of the coronary circulation. When the coronary artery diameter does not change, the CFR is determined as the ratio of the maximum coronary artery blood flow velocity to the coronary artery blood flow velocity at rest because the coronary artery blood flow rate and the coronary artery blood flow velocity are linearly correlated.

The CFR is about 3.0 to about 4.0 in a healthy person example but is less than 2.0 in significant stenosis with a diameter stenosis (% DS) of 75% or more. Moreover, it has been reported that the CFR decreases even in the case of the minimum coronary artery disorder even when the coronary artery does not have significant stenosis. The CFR is not merely used for evaluating the diameter stenosis rate of the coronary artery but as the overall index of the coronary circulation including the coronary microcirculation.

Patent Document 1 discloses a guide wire provided with a pressure sensor having a temperature sensing member at a tip portion. The pressure sensor is provided in a stainless steel outer tube having an opening portion. The temperature sensing member in the pressure sensor is exposed from the stainless steel outer tube through the opening portion. The temperature sensing member outputs signals corresponding to temperature changes associated with mass flow rate changes of the blood flow in contact therewith through the opening portion. Patent Document 1 describes that the CFR can be calculated based on only the output signals of the temperature sensing member.

CITATION LIST

Patent Document

Patent Document 1: Japanese Unexamined Patent Application Publication No. 2000-504249

SUMMARY OF INVENTION

Technical Problem

The temperature sensing member in the guide wire described in Patent Document 1 is in contact with the blood flow through the opening portion of the stainless steel outer tube. Since the temperature sensing member is provided on the outer peripheral surface side of the stainless steel outer tube, the temperature detection member can acquire only information on the mass flow rate of the blood flow near the inner wall of a blood vessel. Since the temperature detection member is provided at a predetermined position in the circumferential direction in the stainless steel outer tube, only the information on the mass flow rate of the blood flow at a predetermined position in the circumferential direction of a blood vessel can be acquired. As a result, with the configuration of the guide wire described in Patent Document 1, there is a possibility that the mass flow rate of the blood flow in a blood vessel cannot be correctly measured.

The present invention has been made in view of the circumstances described above. It is an object of the present invention to provide a blood flow meter and a measurement device capable of acquiring information on the mass flow rate of the blood flow in a blood vessel of a living body with high accuracy.

Solution to Problem (1) A blood flow meter according to the present invention has a hollow shaft which has flexibility and is insertable into a blood vessel, an element holding body which is provided on the distal side of the shaft so as to be coaxial with the shaft and has a tubular shape and an outer diameter smaller than or equal to the outer diameter of the shaft, a flow rate sensor which has a measurement element containing a heating resistor having a temperature-resistance characteristic and is accommodated in the element holding body in a state where the measurement element can detect the temperature changes in the peripheral wall of the element holding body over the entire circumference, and a thermal conductive insulating member disposed between the flow rate sensor and the element holding body in the element holding body.

With such a configuration, the measurement element of the flow rate sensor can detect the temperature changes over the entire circumference in the circumferential direction of the element holding body due to the mass flow rate changes of the blood flow through the insulating member at arbitrary positions in a blood vessel.

(2) Preferably, the heating resistor is a wire rod and, in the measurement element, the wire rod is spirally wound to be formed into a coil shape so that adjacent wire rods are separated and insulated and the measurement element is accommodated in the element holding body along the axial direction of the element holding body.

The measurement element of the coil shape can acquire the temperature changes over the entire circumference of the element holding body over the entire length along the axial direction.

(3) Preferably, the wire rod is a metal wire which is not insulation coated.

Thus, an increase in the outer diameter is prevented in the measurement element of the coil shape, and therefore the measurement element can be accommodated in the element holding body having a predetermined outer diameter.

(4) Preferably, the metal wire is a nickel wire or a platinum wire.

Thus, the mass flow rate changes of the entire blood flow can be acquired with high accuracy by the measurement element.

(5) Preferably, the outer diameter of the shaft is 0.36 mm or less.

Thus, the blood flow meter can be smoothly moved in a blood vessel.

(6) Preferably, the insulating member is a resin having thermal diffusivity of 0.06 to 0.21 $mm^2/s$.

Thus, the measurement element can acquire the temperature changes in the element holding body with good accuracy.

(7) Preferably, the flow rate sensor has an insulating core material and the measurement element is provided on the outer peripheral surface of the core material.

Thus, the measurement element can be formed into a predetermined coil shape.

(8) Preferably, a pair of leads supplying electric power to the measurement element are further provided, one of the pair of leads is inserted into and passed through the inside of the core material, the lead and one end of the measurement element are electrically connected to each other, and the other lead and the other end of the measurement element are electrically connected to each other.

Thus, an increase in the outer diameter is prevented in the measurement element of the coil shape, and therefore the measurement element can be accommodated in the element holding body having a predetermined outer diameter.

(9) Preferably, a coaxial cable supplying electric power to the measurement element is further provided, an internal conductor of the coaxial cable is inserted into and passed through the inside of the core material to be electrically connected to one end of the measurement element, and the other end of the measurement element is electrically connected to an external conductor of the coaxial cable.

Also in this case, an increase in the outer diameter is prevented in the measurement element of the coil shape, and therefore the measurement element can be accommodated in the element holding body having a predetermined outer diameter.

(10) Preferably, a pair of leads connected to end portions of the measurement element are further provided and the measurement element is provided on the circumference of both or either of the leads.

Thus, a special member for holding the measurement element in the coil shape is not required.

(11) Preferably, a coaxial cable supplying electric power to the measurement element is further provided and the measurement element is provided on the outer peripheral surface of an external coating material of the coaxial cable or an internal coating material exposed from the coaxial cable.

Also in this case, a special member for holding the measurement element in the coil shape is not required.

(12) Preferably, a flexible member of a cylindrical shape having flexibility is provided at the distal end of the shaft so as to be coaxial with the shaft and the element holding body is provided at the distal end of the flexible member so as to be coaxial with the flexible member.

Thus, the blood flow meter can be easily moved along a blood vessel.

(13) Preferably, a guide body of a cylindrical shape having flexibility is provided at the distal end of the element holding body so as to be coaxial with the element holding body.

Thus, the blood flow meter can be easily moved to an arbitrary position in a blood vessel.

(14) Preferably, the guide body has a coiled spring containing a radiopaque metal wire.

Thus, the position of the flow rate sensor in a blood vessel can be specified.

(15) A measurement device of the present invention has the blood flow meter described above and a measurement portion supplying electric power to a measurement element of the blood flow meter to acquire information on the mass flow rate of the blood flow from electric power information based on the resistance changes corresponding to the temperature changes of the measurement element.

Thus, the information on the mass flow rate changes of the blood flow can be acquired with high accuracy based on the electric information acquired in the blood flow meter.

Advantageous Effects of Invention

According to the present invention, the information on the mass flow rate of the entire blood flow can be acquired with high accuracy at a desired position in a blood vessel.

DESCRIPTION OF EMBODIMENTS

Hereinafter, preferable embodiments of the present invention are described. The embodiments merely describe one embodiment of the present invention and it is a matter of course that the embodiments can be altered insofar as the gist of the present invention is not altered.

First Embodiment

Figure 1:
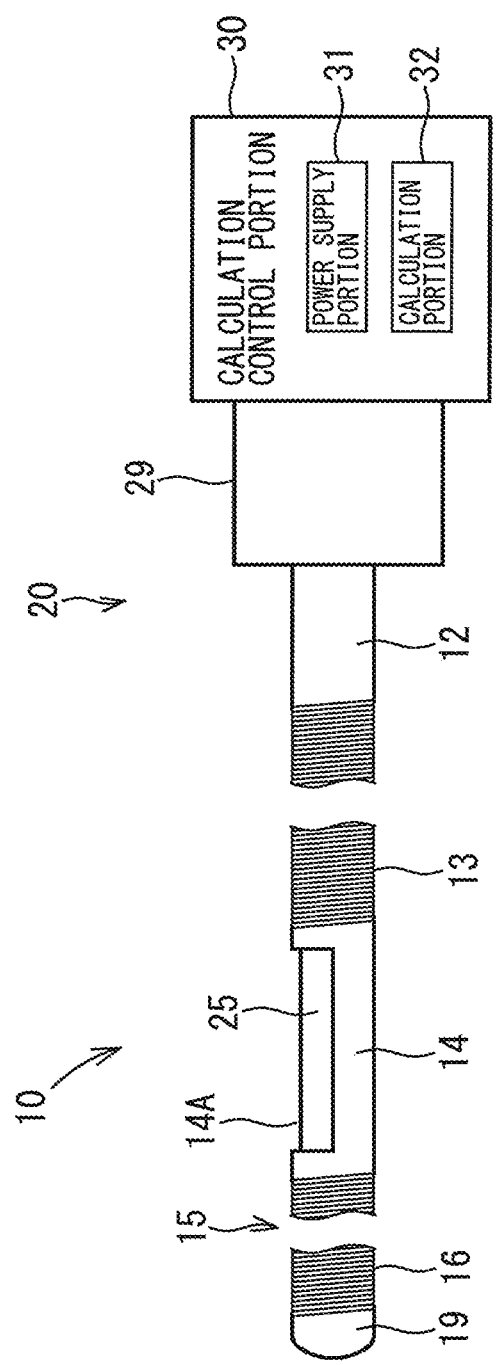
FIG. 1 is a schematic view illustrating the configuration of a measurement device 20 having a blood flow meter 10 according to a first embodiment of the present invention.

As illustrated in FIG. 1, a measurement device 20 has a guide wire type blood flow meter 10 which is insertable into a blood vessel (for example, coronary artery) of a living body and a calculation control portion 30 calculating a value about the mass flow rate of blood based on information acquired by the blood flow meter 10.

The blood flow meter 10 has a hollow shaft 12 having an outer diameter smaller than the diameter of a blood vessel of a living body. At an end portion on the tip side (equivalent to the distal side) of the shaft 12, a flexible member 13 of a cylindrical shape having flexibility with which the flexible member 13 is bent along a blood vessel is provided so as to be coaxial with the shaft 12. The coaxial state is a state where the axial center of each of a plurality of members formed into a columnar shape or a cylindrical shape is positioned on the same line.

At the distal end of the flexible member 13, an element holding body 14 having a tubular shape in which a flow rate sensor 21 of a heat ray type acquiring the information on the mass flow rate of the blood flow in a blood vessel is accommodated is provided so as to be coaxial with the flexible member 13. Furthermore, on the distal side of the element holding body 14, a guide body 15 of a cylindrical shape guiding the blood flow meter 10 in a blood vessel is provided so as to be coaxial with the element holding body 14.

The flexible member 13, the element holding body 14, and the guide body 15 configuring the blood flow meter 10 are configured so that a stainless steel wire rod is spirally wound or so as to contain a stainless steel tubular body. The blood flow meter 10 having the flexible member 13, the element holding body 14, and the guide body 15 has flexibility with which the blood flow meter 10 is bent as a whole along a curve, a branch, and the like of a blood vessel.

Figure 2:
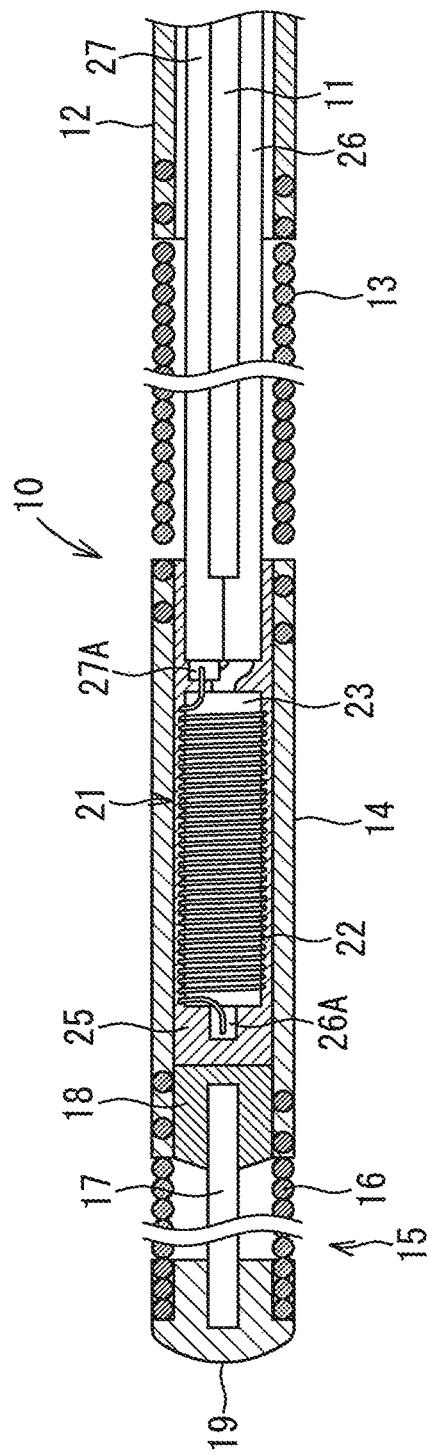
FIG. 2 is a vertical cross-sectional view of a tip portion of the blood flow meter 10.
Figure 3:
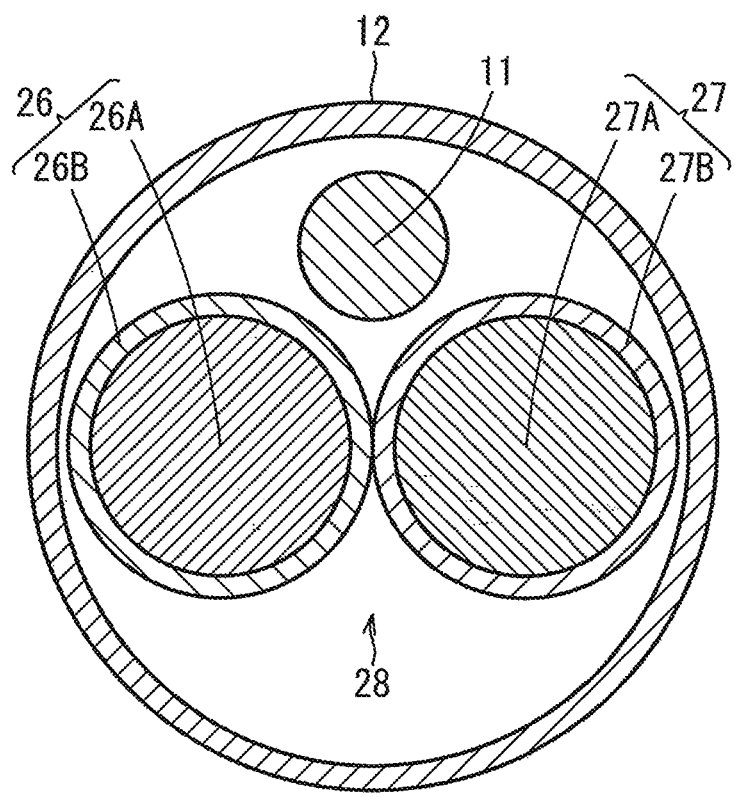
FIG. 3 is a horizontal cross-sectional view of a shaft 12 provided in the blood flow meter 10.

As illustrated in FIG. 2 and FIG. 3, a core wire 11 and a pair of leads 26 and 27 for use in energization or the like to the flow rate sensor 21 (FIG. 2) provided in the element holding body 14 are inserted into and passed through the inside of the shaft 12 along the longitudinal direction of the shaft 12.

The core wire 11 contains stainless steel having a wire diameter smaller than the internal diameter of the shaft 12, for example, and is extended from the proximal side of the shaft 12 to the vicinity of the element holding body 14. The core wire 11 prevents the shaft 12 from being largely bent by selecting one having bending rigidity higher than that of the shaft 12.

As illustrated in FIG. 3, the leads 26 and 27 are those in which copper wires 26A and 27A are insulation coated with insulation coating materials 26B and 27B, such as a polyurethane resin, respectively. As illustrated in FIG. 2, the distal end of one lead 26 (hereinafter referred to as "first lead 26") is extended to the distal side relative to the flow rate sensor 21 (left side relative to the flow rate sensor 21 in FIG. 2). The distal end of the other lead 27 (hereinafter referred to as "second lead 27") is extended to the proximal side relative to the flow rate sensor 21 (right side relative to the flow rate sensor 21 in FIG. 2).

As illustrated in FIG. 1, the proximal end of the shaft 12 is connected to the calculation control portion 30 through a connector 29. The first lead 26 and the second lead 27 inserted into and passed through the shaft 12 are electrically connected to the calculation control portion 30.

As illustrated in FIG. 1, an opening portion 14A is formed in the peripheral wall of the element holding body 14. In the opening portion 14A, the length along the axial direction of the shaft 12 is shorter (for example, about 3 mm) than the length along the axial direction of the flow rate sensor 21 and the length in the circumferential direction is about ½ of the outer diameter of the element holding body 14, for example. The details of the flow rate sensor 21 accommodated in the element holding body 14 are described later.

As illustrated in FIG. 2, the guide body 15 has a coiled spring 16 provided at the distal end of the element holding body 14, a sealing member 18 sealing the internal space on the distal side of the element holding body 14, a distal tip 19 provided at the distal end of the coiled spring 16, and a distal core material 17 provided in the internal space of the coiled spring 16.

In the coiled spring 16, a platinum wire having radiopacity, for example, is spirally wound. The coiled spring 16 has flexibility which allows the coiled spring 16 to bend along a curve of a blood vessel, a branch of a blood vessel, and the like. The coiled spring 16 is integrally bonded to the element holding body 14. The coiled spring 16 containing a radiopaque platinum wire or the like has a function as a marker of a tip portion in the blood flow meter 10. The sealing member 18, the distal tip 19, and the distal core material 17 each are formed of stainless steel, for example. The distal core material 17 is extended along the axis line of the coiled spring 16, integrally bonded to the sealing member 18 on the proximal side, and integrally bonded to the distal tip 19 on the distal side. The distal core material 17 prevents the coiled spring 16 from being largely bent by selecting one having bending rigidity higher than that of the coiled spring 16.

Figure 4:
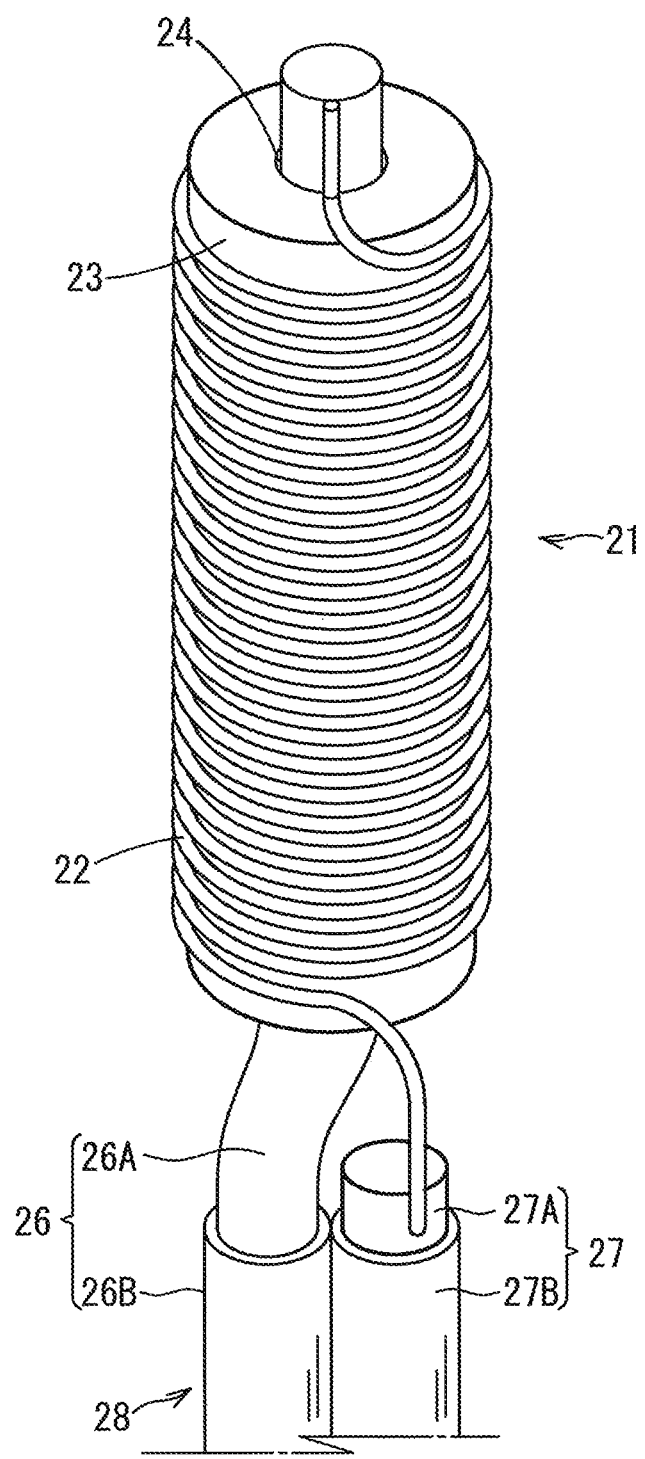
FIG. 4 is a perspective view of a flow rate sensor 21 provided in the blood flow meter 10.

As illustrated in FIG. 4, the flow rate sensor 21 has an insulating core material 23 of a columnar shape and the measurement element 22 formed into a coil shape along the outer peripheral surface of the core material 23.

The core material 23 contains an insulating raw material, such as ceramics. The outer diameter and the length in the axial direction of the core material 23 are set so that the core material 23 can be accommodated in the internal space of the element holding body 14. A through-hole 24 is formed in the center of the core material 23.

The measurement element 22 is an electroconductive heating resistor having a temperature-resistance characteristic. The temperature-resistance characteristic is a characteristic in which the electrical resistance value changes due to temperature changes. Specifically, the measurement element 22 has a characteristic (positive characteristic) in which the electrical resistance value proportionally increases with a temperature increase or a characteristic (negative characteristic) in which the electrical resistance value proportionally decreases with a temperature increase. Therefore, based on the electrical resistance changes in the heating resistor, the temperature changes of the resistance heat generator can be detected.

As the measurement element 22, a nickel wire (positive characteristic) which is not insulation coated is used, for example. The measurement element 22 is spirally wound along the outer peripheral surface of the core material 23 to be formed into a coil shape. In the nickel wire forming the coil shape, adjacent nickel wires are separated so as not to be in contact with each other. Both ends of the coil-shaped nickel wire each are extended to the outside in the axial direction of the core material 23. The nickel wire wound around the outer peripheral surface of the core material 23 is pasted to the outer peripheral surface of the core material 23 with a cyanoacrylate-based instant adhesive or the like, for example.

As illustrated in FIG. 4, the distal end of the second lead 27 is positioned on the proximal side relative to the core material 23. At the distal end of the second lead 27, the copper wire 27A is exposed from the insulation coating material 27B to be electrically connected to one end of the measurement element (nickel wire) 22.

In the other first lead 26, the copper wire 26A is exposed from the insulation coating material 26B on the proximal side relative to the core material 23 and the exposed copper wire 26A is inserted into and passed through the inside of the through-hole 24 of the core material 23. The distal end of the copper wire 26A is positioned on the distal side relative to the core material 23 and is electrically connected to the other end portion of the measurement element (nickel wire) 22.

As illustrated in FIG. 2, the flow rate sensor 21 containing the measurement element 22 and the core material 23 is fixed by an insulating member 25 present between the flow rate sensor 21 and the element holding body 14 in the state of being accommodated in the internal space of the element holding body 14. The insulating member 25 has thermal conductivity and insulation properties. An epoxy resin which is an insulating resin is used, for example. The insulating member 25 covers the entire core material 23 and secures the insulation state of adjacent portions in the axial direction in the nickel wire on the outer peripheral surface of the core material 23. The epoxy resin in a molten state is injected into the internal space of the element holding body 14 from the opening portion 14A formed in the element holding body 14 to be charged into the space between the measurement element 22 and the core material 23 and the element holding body 14. Thereafter, the epoxy resin is cured in the element holding body 14, whereby the measurement element 22 and the core material 23 are fixed in the internal space of the element holding member 14.

As illustrated in FIG. 1, the calculation control portion 30 connected to the blood flow meter 10 has a power supply portion 31 and a calculation portion 32. The power supply portion 31 supplies electric power to the measurement element 22 of the flow rate sensor 21 through the first lead 26 and the second lead 27. The calculation portion 32 calculates a value about the mass flow rate of the blood flow based on the value of a current flowing by the application thereof to the measurement element 22.

[Use Example of Measurement Device 20]

The measurement device 20 is used in order to measure the mass flow rate changes of the blood flow at a predetermined position in the coronary artery, for example. The blood flow meter 10 is inserted into a blood vessel with the distal tip 19 side on the front side, and then sent into a desired position of the coronary artery. The position on the tip side of the blood flow meter 10 in the coronary artery can be grasped based on the position of the guide body 15 in an X-ray fluoroscopic image of the blood vessel.

After the guide body 15 is positioned at a desired position in the coronary artery, a fixed direct current is supplied to the measurement element 22 of the flow rate sensor 21 through the first lead 26 and the second lead 27 from the power supply portion 31 of the calculation control portion 30. The measurement element 22 generates Joule heat by the supply of a current. The Joule heat is transmitted to the element holding body 14 through the insulating member 25. Since blood flows around the outer peripheral surface of the element holding body 14, and therefore the heat of the heated element holding body 14 is taken by the blood, so that the element holding body 14 is cooled. Due to the fact that the element holding body 14 is cooled, the temperature of the measurement element 22 decreases.

In this case, when the mass flow rate of the blood flow changes with the pulsation generated by heartbeats, the quantity of heat taken from the element holding body 14 changes, and, as a result, the temperature changes associated with the pulsation occur also in the measurement element 22. The measurement element 22 contains the heating resistor having the temperature-resistance characteristic, and therefore the electrical resistance changes due to the occurrence of the temperature changes. A fixed direct current is caused to flow in the measurement element 22. Therefore, when the electrical resistance of the measurement element 22 changes, a voltage applied to the measurement element 22 changes. The calculation portion 32 in the calculation control portion 30 calculates a value about the mass flow rate of the blood flow based on such voltage changes in the measurement element 22.

Specifically, when the temperature of the measurement element 22 decreases by the blood flow, the electrical resistance value of the measurement element 22 containing the nickel wire proportionally decreases. As a result, a voltage to be applied to the measurement element 22 decreases. The calculation portion 32 calculates the flow velocity of the blood flow based on the detected voltage reduction, for example.

In the element holding body 14 having a tubular shape, blood flows along the axial direction over the entire outer peripheral surface, and therefore a large heat quantity change occurs to a minute change in the mass flow rate of the blood flow. Thus, the temperature considerably changes also in the measurement element 22 of the flow rate sensor 21, so that the electrical resistance value considerably changes. Therefore, the measurement element 22 can measure the mass flow rate changes of the blood flow flowing through the entire outer peripheral surface of the element holding body 14 along the axial direction.

The nickel wire used as the measurement element 22 of the flow rate sensor 21 is a metal material in which the electric resistivity $\rho$ and the temperature coefficient $\alpha$ each are large and the product ($\rho \cdot \alpha$) of the electric resistivity $\rho$ and the temperature coefficient $\alpha$ is as large as 0.061 ($\mu\Omega \cdot cm/°$ C.). In the measurement element 22 containing such a nickel wire, a change in the electrical resistance value to the temperature change per 1° C. is large. Since such a nickel wire is wound in a coil shape, the measurement element 22 faces the inner peripheral surface of the element holding body 14 without interruption in the circumferential direction. Thus, the measurement element 22 can detect the temperature changes over the entire circumference of the peripheral wall of the element holding body 14 with the entire nickel wire.

Thus, the measurement element 22 can measure the mass flow rate changes of the entire blood flow in a blood vessel with high accuracy.

It is preferable that the blood flow meter 10 in this embodiment is provided with the flexible member 13, the element holding body 14, and the guide body 15 having the same outer diameter as the outer diameter of the shaft 12 in the tip portion of the shaft 12 having an outer diameter set to 0.35 mm, so that the entire outer diameter is smaller than 0.36 mm. The 0.36 mm outer diameter in this case is a standard value on the outer diameter of a guide wire usable for the coronary artery. Due to the fact that the outer diameters of the shaft 12 and the like are set as described above, the blood flow meter 10 is suitably used for measuring the mass flow rate of the blood flow in the coronary artery.

[Characteristics of Flow Rate Sensor 21]

Hereinafter, the characteristics of the flow rate sensor 21 are described.

In order to acquire information on the mass flow rate changes in the blood flow by the blood flow meter 10, the flow rate sensor 21 preferably has the time response characteristics (time constant) capable of measuring the flow velocity changes due to pulsation. Thus, the time response characteristics (time constant) of the flow rate sensor 21 in the blood flow meter 10 were simulated by measuring the flow velocity changes of a water current imitating the pulsation generated by the circulation of the blood flow of the living body temperature using a flow rate sensor (Type C) corresponding to the flow rate sensor 21.

The flow rate sensor of Type C has a measurement element in which a nickel wire having a wire diameter of 0.0095 mm is spirally wound around the insulating core material 23 to be formed into a coil shape and the flow rate sensor has an outer diameter which allows the flow rate sensor to be accommodated in a 0.35 mm element holding body.

Moreover, for comparison, two flow rate sensors each having an outer diameter set to be larger than that of the flow rate sensor of Type C are prepared with a nickel wire having a wire diameter of 0.014 mm, and then the flow velocity changes of the pulsation were measured in the same manner as in the flow rate sensor of Type C. The outer diameter of one flow rate sensor is set to an outer diameter which allows the flow rate sensor to be accommodated in an element holding body having an outer diameter of 1.1 mm (Type A). The outer diameter of the other flow rate sensor is set to an outer diameter which allows the flow rate sensor to be accommodated in an element holding body having an outer diameter of 0.6 mm (Type B). The conditions (the outer diameter of the element holding body 14 and the wire diameter of the nickel wire) of the flow rate sensors of Type A, Type B, and Type C are shown in Table 1.

TABLE 1

| Flow rate sensor | Outer diameter of element holding body | Wire diameter of nickel wire |
| --- | --- | --- |
| Type A | ϕ1.1 mm | ϕ0.014 mm |
| Type B | ϕ0.6 mm | ϕ0.014 mm |
| Type C | ϕ0.36 mm | ϕ0.0095 mm |

The pulsation imitating the circulation of the blood flow of the living body temperature was generated by providing a circulation water path in a 37° C. constant-temperature water bath, and then supplying a water current to the circulation water path by a roller pump. The water current was pulsated with an about 0.5 (1/s) cycle by the rotation of the roller pump. In the middle of such a circulation water path, a pipe having an internal diameter of 2.0 mm was provided as a measurement flow path. The flow velocity of the water current in the measurement flow path was measured with each of the above-described three types of flow rate sensors. Fixed currents of 20 mA and 30 mA were supplied to the measurement element of each flow rate sensor to cause self-heating, and then voltage changes generated in the measurement element was amplified with a differential amplifier and recorded using a digital pen recorder for each current. The voltage changes (output waveform of the flow rate sensor) of the measurement element were recorded for two cases of a case where a 400 Hz low pass filter was present and a case where a low pass filter was not present.

In order to obtain the reference (reference value) of the pulsation of the water current in the circulation water path, Coriolis mass flowmeter (manufactured by KEYENCE CORP., Trade name "FD-SS 2A", Response time of 50 ms) was disposed in the middle of a measurement water path, and the mass flow rate in the measurement water path was measured. Then, the waveform obtained by dividing the mass flow rate (ml/s) obtained by the Coriolis mass flowmeter with the cross section area of the measurement flow path (pipe) was defined as the reference waveform corresponding to the flow velocity value (mm/s) in the measurement flow path.

Figure 5:
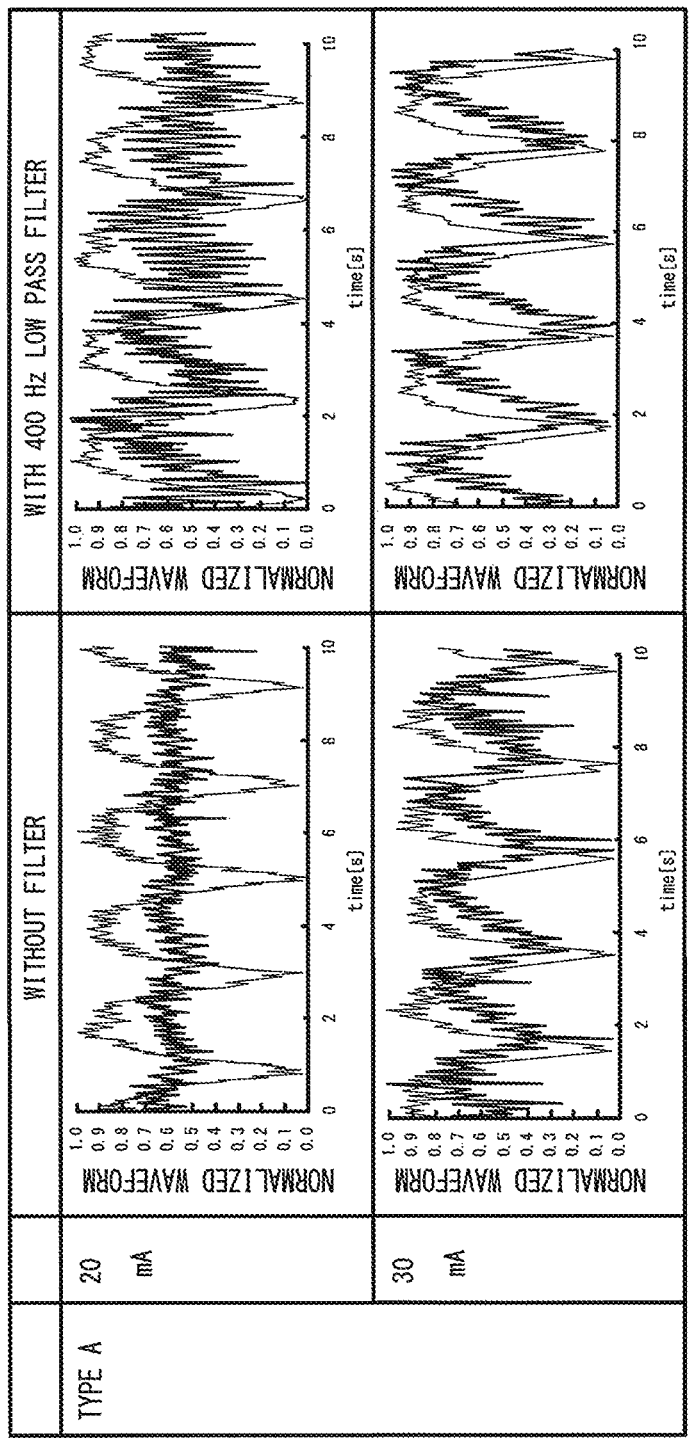
FIG. 5 is a graph showing the results obtained by simulating the time responsibility of the measurement element by a flow rate sensor of Type A.
Figure 6:
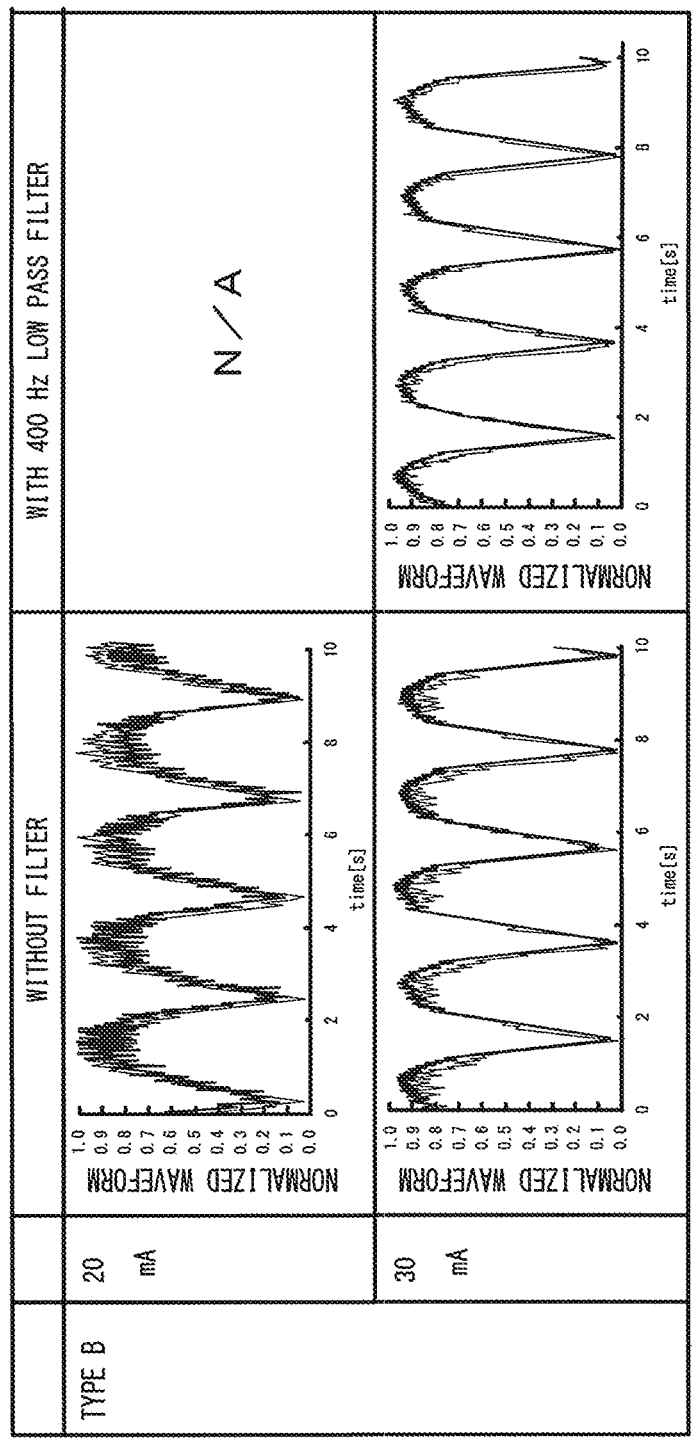
FIG. 6 is a graph showing the results obtained by simulating the time responsibility of the measurement element by a flow rate sensor of Type B.
Figure 7:
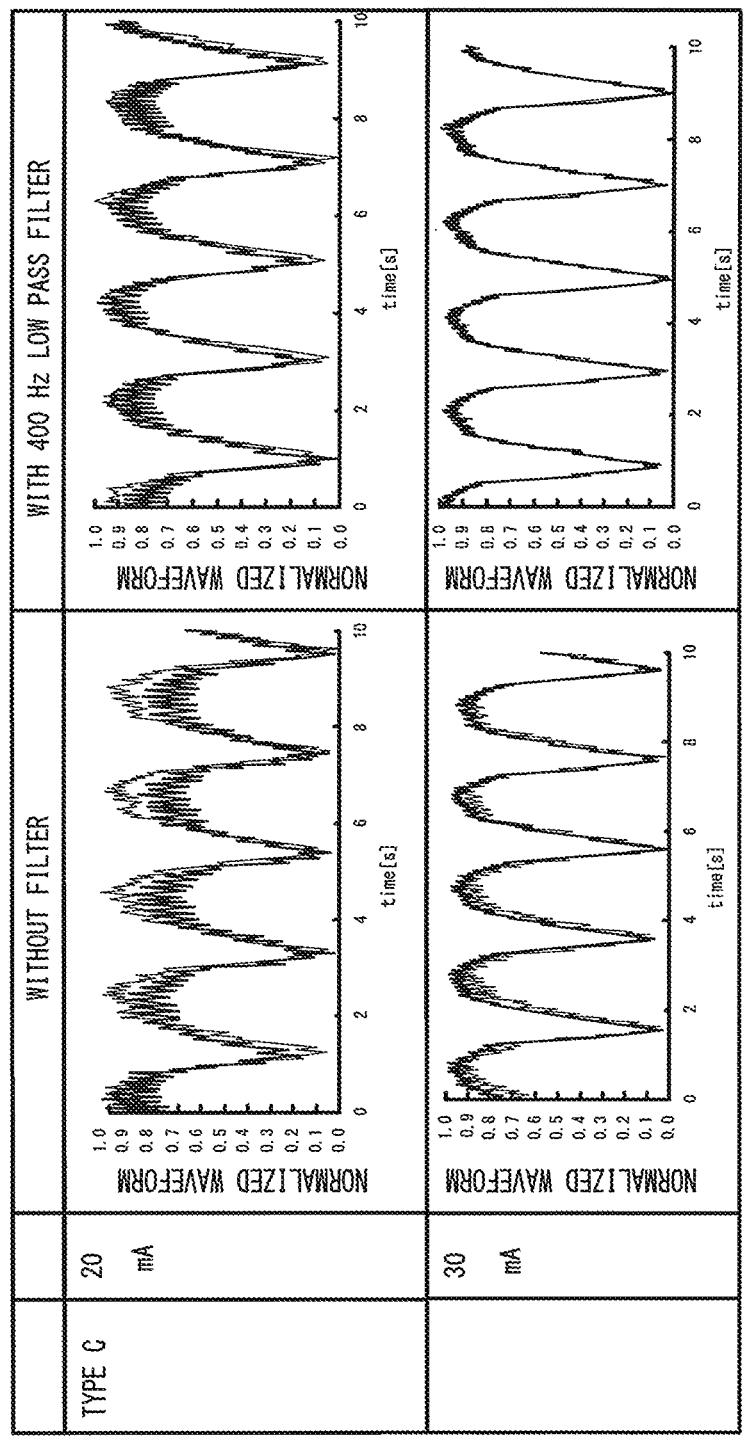
FIG. 7 is a graph showing the results obtained by simulating the time responsibility of the measurement element by a flow rate sensor of Type C.

In order to verify the similarity of the output waveforms (two kinds) of each of the flow rate sensors of Type A, Type B, and Type C and the reference waveform, each output waveform and the reference waveform were normalized and overlapped with each other. The results are illustrated in FIG. 5, FIG. 6, and FIG. 7. Each of FIG. 5, FIG. 6, and FIG. 7 is the graph in which the normalized output waveforms (thick line) corresponding to the voltage changes of each of the flow rate sensors of Type A, Type B, and Type C and the reference waveform (thin line) are overlapped with each other.

As illustrated in FIG. 5, the similarity to the reference waveform of the output waveforms of the flow rate sensor of Type A was low irrespective of the presence of the low pass filter, so that the flow velocity of the pulsation in the water current was not able to be reproduced. On the other hand, as illustrated in FIG. 6, the similarity to the reference waveform of the output waveforms of the flow rate sensor of Type B was high when the low pass filter was present (data was not obtained for the case where the low pass filter was not present), so that the flow velocity of the pulsation in the water current was able to be reproduced. Furthermore, as illustrated in FIG. 7, the similarity to the reference waveform of the output waveforms of the flow rate sensor of Type C was high irrespective of the presence of the low pass filter, so that the flow velocity of the pulsation in the water current was able to be reproduced with high accuracy.

The results above are considered to result from the fact that, when a nickel wire with a large wire diameter is used in order to increase the outer diameter of the measurement element of the coil shape, the resistance value changes to the temperature changes of the nickel wire decrease, which leads to a reduction in the time response characteristics (time constant) of the heating resistor in the measurement element. More specifically, it is considered that, when the time constant of the heating resistor which is the measurement element decreases, the electrical resistance value changes cannot follow the temperature changes generated by the pulsation of the water current, so that a voltage corresponding to the pulsation cannot be output.

In the output waveforms of the flow rate sensors of Type A, Type B, and Type C illustrated in FIG. 5, FIG. 6, and FIG. 7, respectively, the noise is smaller in the case of supplying the 30 mA current than the case of supplying the 20 mA current. Therefore, when the mass flow rate changes in the blood flow are measured, it is preferable to set the current to be supplied to the measurement element of the flow rate sensor to be high. However, even in the case where a relatively low current is supplied to the measurement element, a noise can be reduced by the adjustment of the amplification degree and the like of the differential amplifier.

Next, the time response characteristics when the three flow rate sensors of Type A, Type B, and Type C were disposed in the blood flow in the coronary artery were verified. For the verification, using three blood flow meters provided with the flow rate sensors of Type A, Type B, and Type C, each flow rate sensor was positioned in the coronary artery of a domestic pig (Female, 30000 g), and then the output waveforms of the flow rate sensors were individually recorded.

Figure 8:
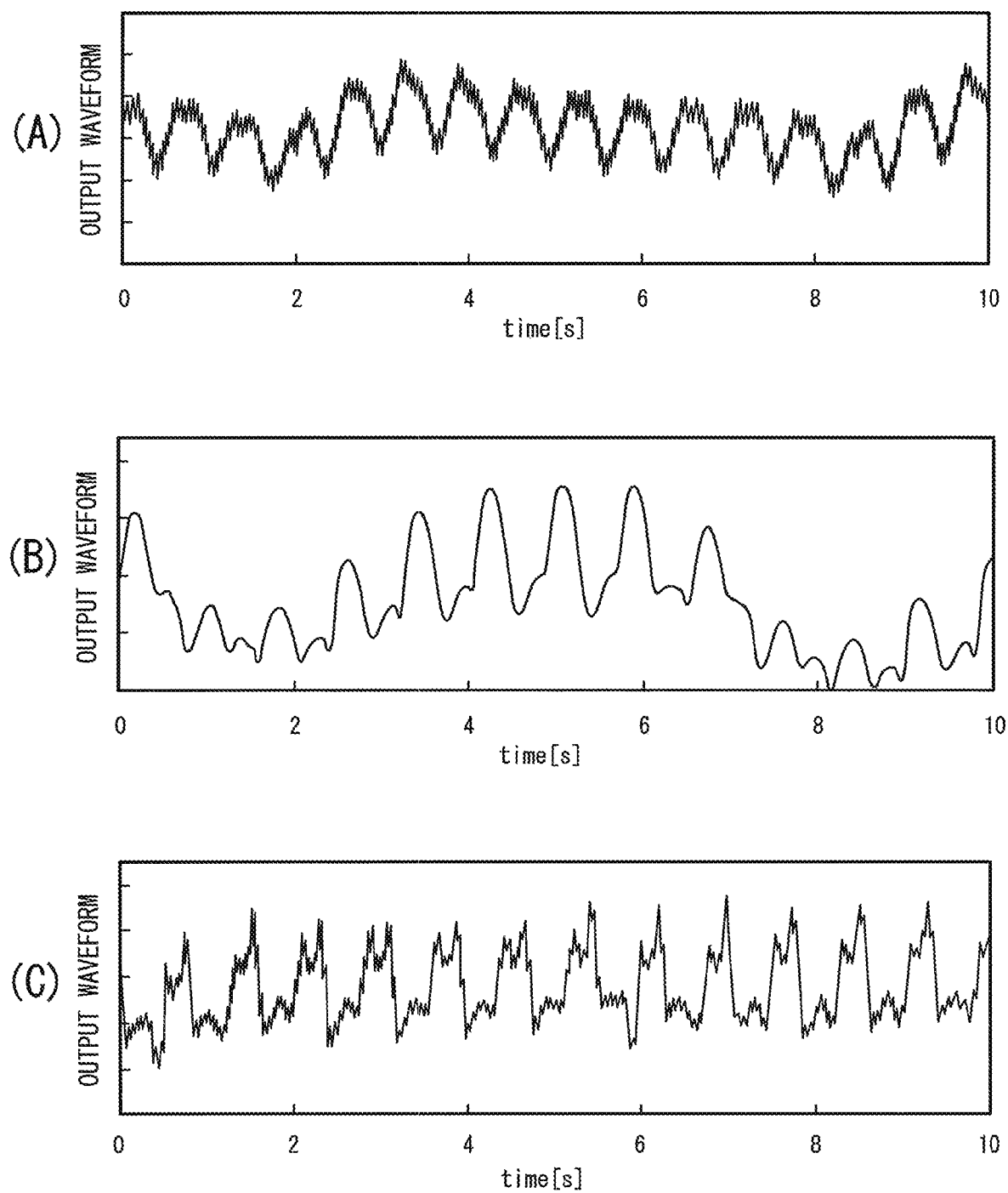
FIGS. 8(A), 8(B), and 8(C) of FIG. 8 each are a graph showing the output waveform when each of the flow rate sensors of Type A, Type B, and Type C is disposed in the blood flow of the coronary artery of a living body.

The output waveforms of the flow rate sensors of Type A, Type B, and Type C are illustrated in FIGS. 8(A), 8(B), and 8(C), respectively. In the output waveforms of all of the flow rate sensors, the bimodal flow velocity corresponding to the diastole and the systole of the heart was measured. Also in all the output waveforms, the respiratory fluctuations (0.5 to 3 Hz) of the blood flow appeared. Particularly in the output waveform of the flow rate sensor of Type C illustrated in FIG. 8(C), the flow velocity changes corresponding to the actual diastole and the actual systole of the heart was faithfully reproduced. This is considered to be because the time constant of the heating resistor in the measurement element decreased with a reduction in the wire diameter of the nickel wire, so that the measurable frequency band in the pulsation increased.

As described above, it was verified that the flow rate sensor 21 corresponding to the flow rate sensor of Type C has a time constant capable of measuring the flow velocity changes of the blood flow in the coronary artery of a living body with high accuracy.

[Thermal Conductivity of Insulating Member]

In the first embodiment, the flow rate sensor 21 accommodated in the element holding body 14 is covered with the insulating member 25, and therefore the heat quantity changes of the element holding body 14 based on the mass flow rate changes corresponding to the pulsation of the blood flow are transmitted to the measurement element 22 through the insulating member 25. Therefore, depending on the thermal conductivity of the insulating member 25, the timing of the temperature changes of the measurement element 22 considerably shift to the mass flow rate changes by the pulsation of the blood flow, and the measurement element 22 may not be able to measure the mass flow rate changes by the pulsation of the blood flow with good accuracy.

When the timing of the temperature changes in the measurement element 22 shifts depending on the thermal conductivity of the insulating member 25, the output timing of electric signals from the measurement element 22 also shifts. In this case, the actual time constant of the measurement element 22 does not change but it can be considered that the apparent time response characteristics (time constant) of the measurement element 22 change.

Thus, the apparent time response characteristics of the measurement element 22 were simulated based on the thermal property values of the insulating member 25.

In this simulation, assuming a case where five kinds of insulating resin including epoxy were used as the insulating member 25 in the configuration of the blood flow meter 10, the apparent time constant of each measurement element 22 was calculated based on the thermal property values of each insulating resin. Four kinds of the insulating resin other than the epoxy are silicone, polyamide, polyimide, and high-density polyethylene. The thermal property values of the insulating resin are density, specific heat, thermal conductivity, and thermal diffusivity. Table 2 shows the thermal property values of each insulating resin mentioned above and the calculated apparent time constant of the measurement element 22.

TABLE 2

| Insulating resin type | Thermal property values | | | | Simulation results Apparent time constant (1/e) [s] |
|---|---|---|---|---|---|
| | Density [g/mm$^3$] | Specific heat [J/gK] | Thermal conductivity [W/mmK] | Thermal diffusivity [mm$^2$/s] | |
| Silicone | 2.20E−03 | 1.20 | 1.70E−04 | 0.06 | 0.023 |
| Polyamide | 1.12E−03 | 1.59 | 2.50E−04 | 0.14 | 0.014 |
| Epoxy | 1.85E−03 | 1.10 | 3.60E−04 | 0.18 | 0.012 |
| Polyimide | 1.40E−03 | 1.13 | 3.40E−04 | 0.21 | 0.011 |
| High-density polyethylene | 9.40E−04 | 2.30 | 5.00E−04 | 0.23 | 0.010 |

As shown in Table 2, when the thermal property values of the insulating resin used for the insulating member 25 change, the apparent time constant in the measurement element 22 changes. Thus, the mass flow rate changes based on the pulsation of the blood flow are detectable with high accuracy by selecting and using an insulating resin having suitable thermal property values corresponding to the physical properties and the like of the blood flow as the insulating member 25.

When the insulating resin is used as the insulating member 25, the thermal property values of the insulating resin can be changed by mixing a conductive substance and the like in the insulating resin. For example, when metal powder is mixed in the insulating resin, the thermal diffusivity of the insulating resin increases. Thus, when the insulating resin is used as the insulating member 25, the apparent time constant in the measurement element 22 can be changed by mixing conductive substances, such as metal powder, in the insulating resin.

For example, in order to detect a frequency component 10 times or more the cardiac output cycle (Main cycle of blood flow fluctuations, usually 1.1 to 2.0 Hz) by the measurement element 22, the detection of 20 Hz or more frequency components is required. Therefore, it is necessary to set the apparent time constant (s) of the measurement element 22 to be 1/20 (=0.05) or lower. Thus, an insulating resin with a predetermined high thermal diffusivity value in which the apparent time constant in the measurement element 22 is 0.05 or less or an insulating resin adjusted to a predetermined high thermal diffusivity value by mixing of a conductive substance is usable as the insulating member 25. On the contrary, when the measurement results in which the influence of the cardiac output cycle is eliminated and the flow velocity changes are averaged are required, an insulating resin having low thermal diffusivity or an insulating resin having thermal diffusivity adjusted to be low is usable as the insulating member 25.

When the flow velocity of the blood flow is high, the changes in the flow velocity per unit time increase. Therefore, the temperature changes per unit time in the element holding body 14 also increase. Therefore, when the thermal diffusivity of the insulating member 25 increases, the temperature changes per unit time in the element holding body 14 are diffused by the insulating member 25, so that the temperature changes in the measurement element 22 decrease. Thus, when insulating resins different in thermal diffusivity are used as the insulating member 25, the influence on the temperature changes in the measurement element 22 caused by the flow velocity changes of the blood flow was verified by simulation.

Figure 9:
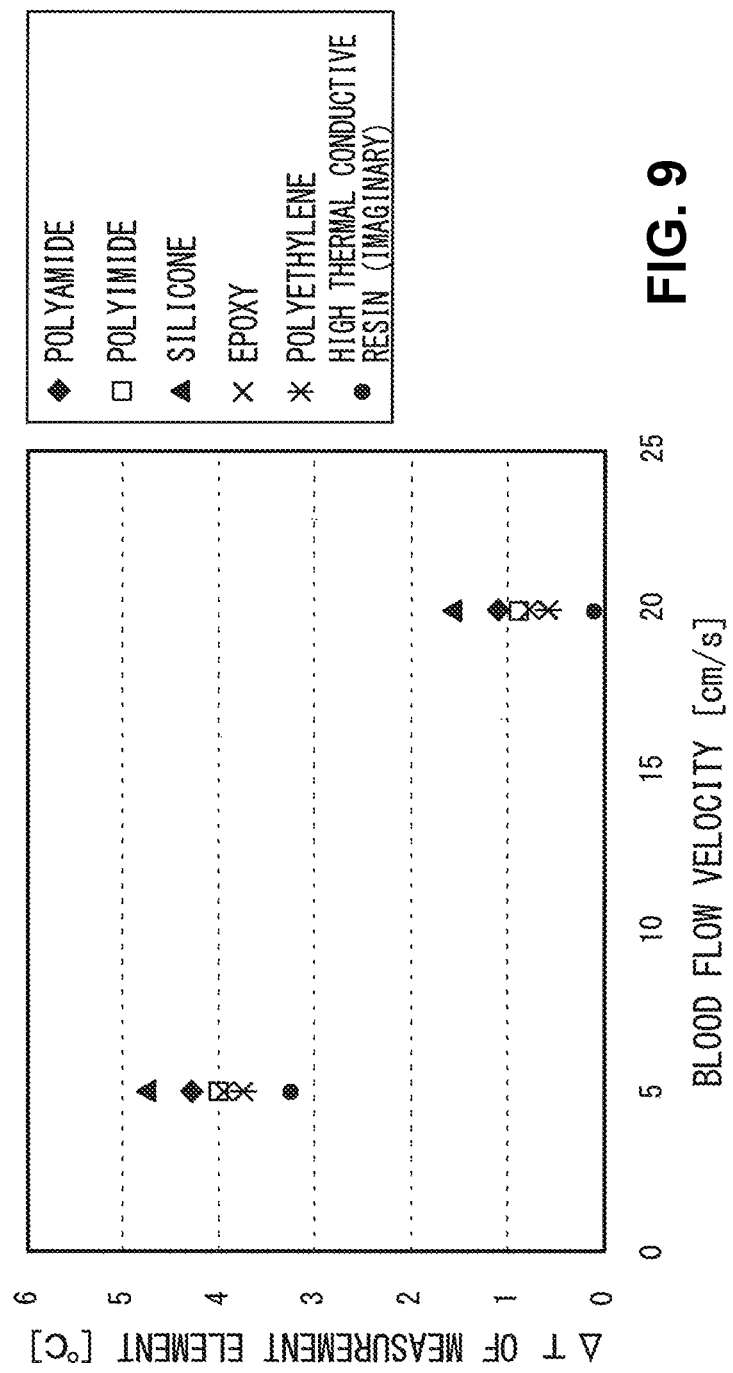
FIG. 9 is a graph showing the results of, in the case of using flow rate sensors fixed in the element holding body by five insulating members having different thermal property values, simulating the temperature changes generated in the measurement element of each of the flow rate sensors due to the flow velocity changes of the blood flow.

In this simulation, when each flow rate sensor 21 in the state of being fixed in the element holding body 14 by the insulating member 25 containing the five kinds of insulating resin was disposed in the blood flow having a flow velocity of 5 cm/s and in the blood flow having a flow velocity of 20 cm/s, the theoretical values of the temperature changes generated in the measurement element 22 caused by the changes in the flow velocity were calculated. The results are illustrated in FIG. 9. Also about the flow rate sensor 21 when an imaginary resin having thermal conductivity higher than that of the five kinds of resin (referred to as "high thermal conductive resin") was used as the insulating member 25, the theoretical value of the temperature changes of the measurement element 22 was calculated by the same simulation. The results are also illustrated in FIG. 9.

As illustrated in FIG. 9, when the five kinds of insulating resin and the imaginary high thermal conductive resin were used as the insulating member 25, the range of the temperature changes generated in the measurement element 22 was about 3 to 5° C. when the flow velocity of the blood flow was 5 cm/s. Therefore, even when any one of the five kinds of insulating resin is used as the insulating member 25, the measurement of the flow velocity changes in the blood flow having a flow velocity of about 5 cm/s can be achieved by the measurement element 22 of this embodiment.

On the other hand, when the flow velocity was 20 cm/s, in the case where the five kinds of insulating resin other than the imaginary high thermal conductive resin was used as the insulating member 25, the temperature changes of the measurement elements 22 was about 0.5° C. to about 1.5° C. When such temperature changes occur, the measurement elements 22 can also measure the flow velocity changes in the blood flow having a flow velocity of about 20 cm/s. However, with the measurement element 22 containing the imaginary high thermal conductive resin, the temperature changes are hardly observed, so that the flow velocity changes in the blood flow having a flow velocity of about 20 cm/s may be unmeasurable.

As described above, all the five kinds of insulating resins (except imaginary high thermal conductive resin) shown in Table 2 are suitably usable as the insulating member 25. Thus, the thermal diffusivity of the insulating resin used as the insulating member 25 is preferably in the range of the thermal diffusivities of all the insulating resin shown in Table 2, i.e., the range of 0.06 to 0.23 mm²/s.

As the insulating member 25, materials having the optimal thermal property values to the properties of a blood vessel to be measured, the physical properties of the blood flow, and the like may be selected. Thus, a configuration using inorganic insulating material powder, such as magnesium, alumina, and silica, is used, without being limited to the insulating resin, as the insulating member 25 may be acceptable. When the inorganic insulating material powder is used, the inorganic insulating material powder may be charged from the opening portion 14A into the element holding body 14 accommodating the flow rate sensor 21 therein, and then the opening portion 14A may be sealed with resin or the like.

Operational Effects of First Embodiment

With the blood flow meter 10 according to the first embodiment, the mass flow rate changes of the blood flow at arbitrary positions of the coronary artery are measurable with high accuracy by the flow rate sensor 21 positioned near the distal end. Therefore, the measurement results obtained by the blood flow meter 10 are appropriately usable as the overall index (CFR) in the coronary artery.

In the measurement element 22, a wire rod, such as a nickel wire or a platinum wire, is spirally wound to be formed into a coil shape so that adjacent wire rods are separated and insulated and the measurement element 22 is accommodated along the axial direction of the element holding body 14 in the element holding body 14. Thus, the measurement element 22 of the coil shape can acquire the temperature changes over the entire circumference of the element holding body 14 over the entire length along the axial direction.

Furthermore, the wire rod configuring the resistance heating element is a metal wire which is not insulation coated, and therefore an increase in the outer diameter of the measurement element 22 of the coil shape is prevented. Thus, the measurement element 22 can be accommodated in the element holding body 14 having a predetermined outer diameter.

Due to the fact that the measurement element 22 contains a nickel wire or a platinum wire, the mass flow rate changes of the entire blood flow can be acquired with high accuracy.

In the first embodiment, in the case where the outer diameter of the shaft 12 is set to 0.36 mm or less, the blood flow meter 10 is configured to have the same size as that of a guide wire for use in a catheter, and therefore the blood flow meter 10 is usable as a guide wire of the catheter. Thus, the blood flow meter 10 can be smoothly moved in a blood vessel.

When the insulating member 25 is a resin having thermal diffusivity of 0.06 to 0.23 mm²/s, the temperature changes of the element holding body 14 based on the flow velocity changes of the blood flow can be measured as the temperature changes in the measurement element 22. Thus, the flow velocity changes of the blood flow can be acquired with good accuracy by the measurement element 22.

Furthermore, the flow rate sensor 21 has the insulating core material 23 and the measurement element 22 is provided on the outer peripheral surface of the core material 23, and therefore the measurement element 22 can be formed into a coil shape having a predetermined outer diameter.

The first lead 26 supplying electric power to the measurement element 22 is inserted into and passed through the inside of the core material 23 to be electrically connected to one end portion of the measurement element 22 and the second lead 27 and the other end portion of the measurement element 22 are electrically connected to each other. Thus, an increase in the outer diameter is prevented in the measurement element 22 of the coil shape, the measurement element 22 can be accommodated in the element holding body 14 having a predetermined outer diameter.

In the first embodiment described above, the flexible member 13 of a cylindrical shape having flexibility is provided at the distal end of the shaft 12 so as to be coaxial with the shaft 12 and the element holding body 14 is provided at the distal end of the flexible member 13 so as to be coaxial with the flexible member 13. Thus, the blood flow meter 10 can be smoothly moved along a blood vessel.

Furthermore, due to the fact that the guide body 15 of a cylindrical shape having flexibility is provided at the distal end of the element holding body 14 so as to be coaxial with the element holding body 14, the blood flow meter 10 can be easily moved to arbitrary positions in a blood vessel.

Due to the fact that the guide body 15 has the coiled spring 16 containing a radiopaque metal (platinum) wire, the position of the flow rate sensor 21 in a blood vessel can be specified.

Second Embodiment

Figure 10:
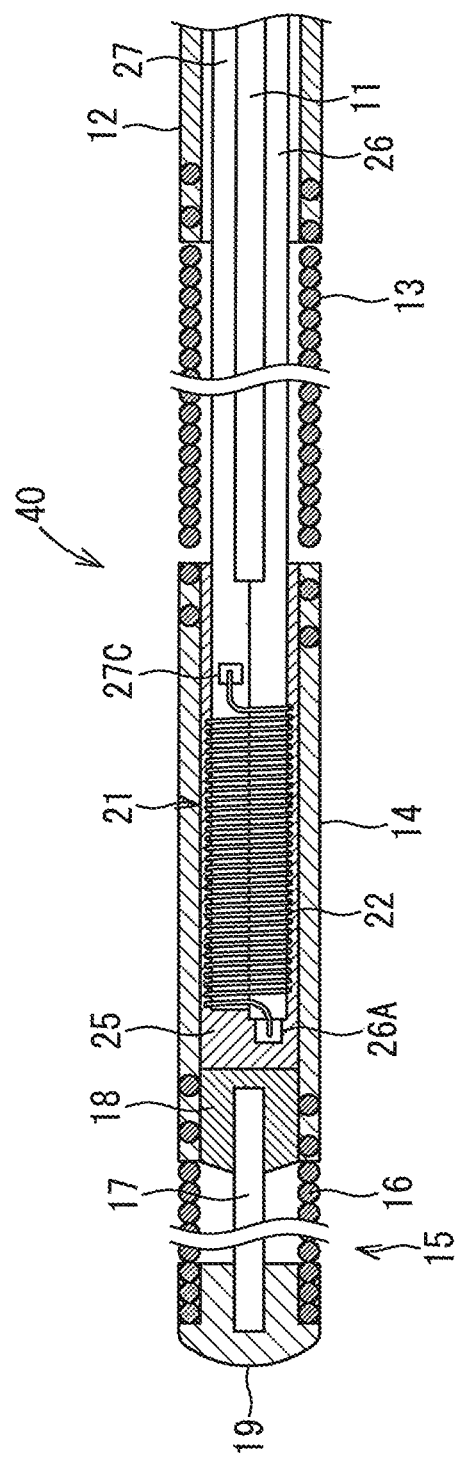
FIG. 10 is a vertical cross-sectional view of a tip portion of a blood flow meter 40 according to a second embodiment.

FIG. 10 is a vertical cross-sectional view of an end portion on the distal side of a blood flow meter 40 of a second embodiment. In the blood flow meter 40 of the second embodiment, a pair of first lead 26 and second lead 27 passing through the inside of a shaft 12 pass through the inside of a flexible member 13 to enter the inside of an element holding body 14, so that the distal end of each of the first lead 26 and the second lead 27 is positioned in an end portion on the distal side of the element holding body 14.

Figure 11:
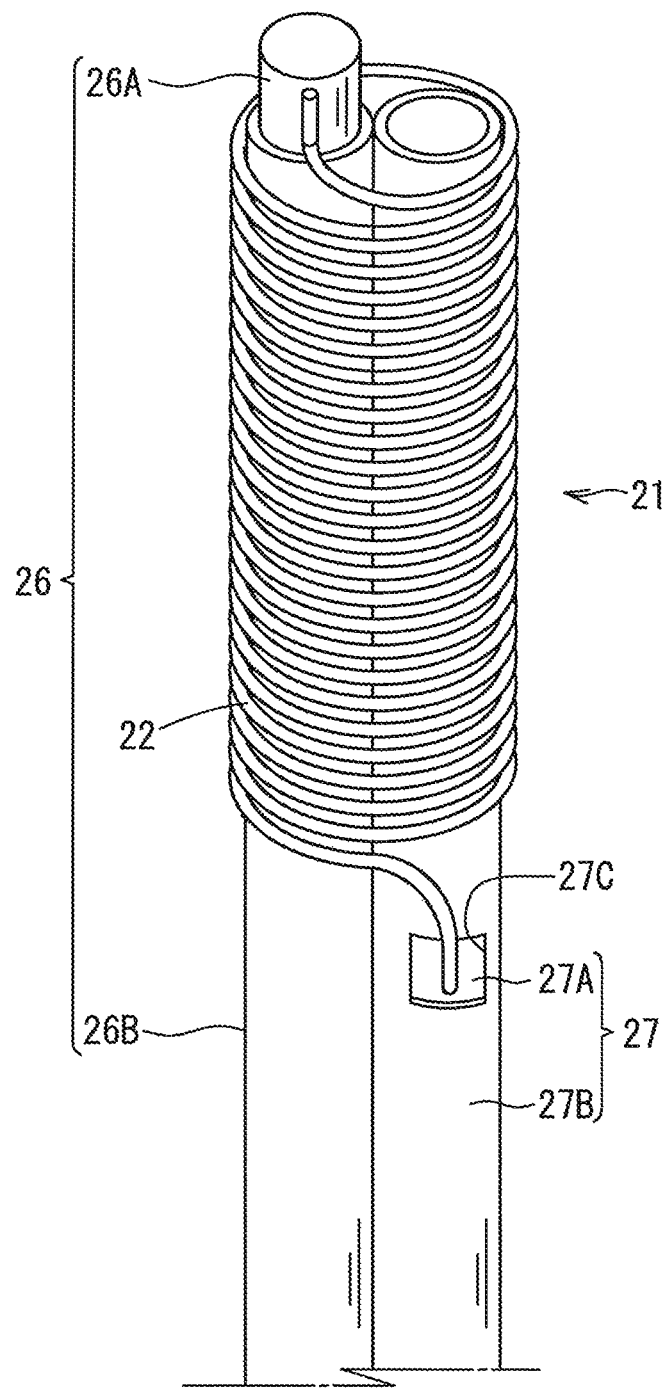
FIG. 11 is a perspective view of a flow rate sensor 21 provided in the blood flow meter 40.

FIG. 11 is a perspective view of a flow rate sensor 21 accommodated in the element holding body 14. The flow rate sensor 21 is not provided with a core material 23 provided in the flow rate sensor 21 of the first embodiment. In a measurement element 22, a nickel wire is spirally wound around the pair of first lead 26 and second lead 27 which are inserted into and passed through the inside of the element holding body 14 to be formed into a coil shape.

In the measurement element 22 having the coil shape, adjacent nickel wires are separated so as not to be in contact with each other as with the first embodiment. The nickel wire wound around the first lead 26 and the second lead 27 is pasted to insulation coating materials 26B and 27B of the first lead 26 and the second lead 27, respectively, with an instant adhesive, for example.

The distal end of each of the first lead 26 and the second lead 27 is positioned on the distal side relative to the measurement element 22 of the coil shape. In the first lead 26, which is one of the leads, the copper wire 26A is exposed from the insulation coating material 26B at the distal end to be electrically connected to one end of the measurement element 22.

In the insulation coating material 27B of the second copper wire 27, which is the other lead, an opening portion 27C is formed on the proximal side relative to the measurement element 22 of the coil shape and a copper wire 27A is partially exposed from the opening portion 27C. The copper wire 27A exposed from the opening portion 27C is electrically connected to the other end of the measurement element 22.

As illustrated in FIG. 10, the pair of first lead 26 and second lead 27 which are inserted into and passed through the inside of the element holding body 14 are fixed with the flow rate sensor 21 by an insulating member 25 provided in the element holding body 14. The insulating member 25 is formed by charging an epoxy resin in a molten state into the element holding body 14, and then curing the same, for example, as with the first embodiment.

Also with the blood flow meter 40 of such a configuration according to the second embodiment, the mass flow rate changes of the blood flow at arbitrary positions of the coronary artery are detectable with high accuracy as with the blood flow meter 10 according to the first embodiment.

In the blood flow meter 40 according to the second embodiment, the measurement element 22 of the flow rate sensor 21 is wound around the pair of first lead 26 and second lead 27 to be formed into the coil shape, and therefore the core material 23 for winding the measurement element 22 of the coil shape in the first embodiment is not required to use. Thus, the number of parts configuring the flow rate sensor 21 decreases, so that the manufacturing cost can be reduced. Moreover, an increase in the outer diameter of the measurement element 22 is prevented, and therefore the measurement element 22 can be accommodated in the element holding body having a predetermined outer diameter.

In the second embodiment, both the first lead 26 and the second lead 27 are inserted into and passed through the inside of the element holding body 14, and then the nickel wire is wound around the first lead 26 and the second lead 27, whereby the measurement element 22 is formed into the coil shape. However, the present invention is not limited to such a configuration and only either the first lead 26 or the second lead 27 may be inserted into and passed through the inside of the element holding body 14, and then a nickel wire may be wound around the lead, whereby the measurement element 22 may be formed into the coil shape.

Third Embodiment

Figure 12:
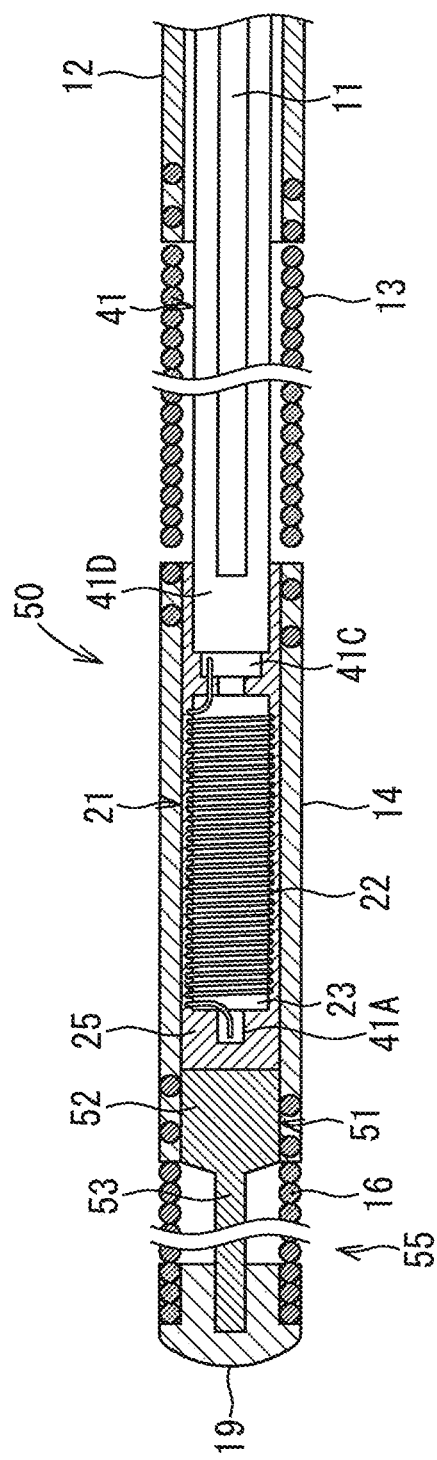
FIG. 12 is a vertical cross-sectional view of a tip portion of a blood flow meter 50 according to a third embodiment.
Figure 13:
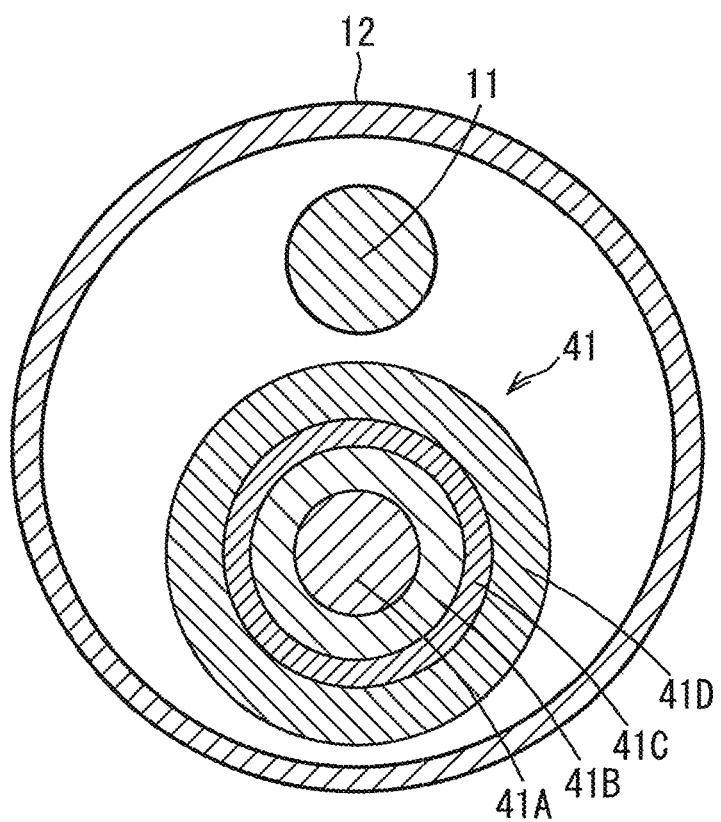
FIG. 13 is a horizontal cross-sectional view of a shaft 12 provided in the blood flow meter 50.

FIG. 12 is a vertical cross-sectional view of a tip portion of a blood flow meter 50 according to a third embodiment. FIG. 13 is a horizontal cross-sectional view of a shaft 12 in the blood flow meter 50. The blood flow meter 50 is configured so that a coaxial cable 41 is inserted into and passed through the inside of the shaft 12 along a core wire 11 and that a current is supplied to a measurement element 22 of a flow rate sensor 21 provided in an element holding body 14 by the coaxial cable 41.

As illustrated in FIG. 13, the coaxial cable 41 has an internal conductor 41A provided in an axial center portion, an internal coating material 41B insulation coating the outer peripheral surface of the internal conductor 41A, an external conductor 41C laminated with a fixed thickness on the outer peripheral surface of the internal coating material 41B, and an external coating material 41D covering the outer peripheral surface of the external conductor 41C. Each of the internal conductor 41A, the internal coating material 41B, the external conductor 41C, and the external coating material 41D is in the coaxial state.

The internal conductor 41A contains an alloy containing copper as the main component. The internal coating material 41B contains fluororesin. The external conductor 41C contains copper foil. The external coating material 41D contains polyurethane resin.

Figure 14:
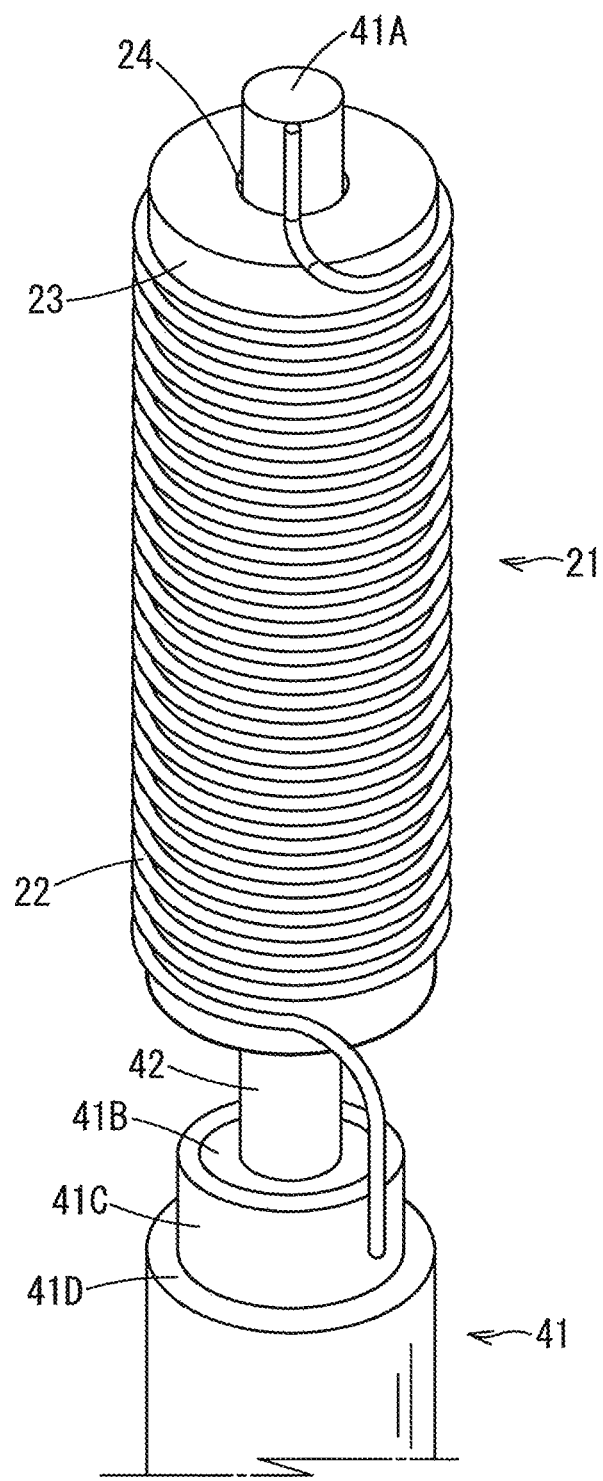
FIG. 14 is a perspective view of a flow rate sensor 21 provided in the blood flow meter 50.

FIG. 14 is a perspective view of the flow rate sensor 21 provided in the element holding body 14. As illustrated in FIG. 14, the flow rate sensor 21 is provided with a measurement element 22 having a coil shape on the outer peripheral surface of a ceramic core material 23 formed in a columnar shape as with the flow rate sensor 21 of the first embodiment. The measurement element 22 contains a nickel wire and is pasted to the outer peripheral surface of the core material 23 with an instant adhesive, for example, so that adjacent nickel wires are separated so as not to be in contact with each other. The flow rate sensor 21 is fixed in the element holding body 14 by the insulating member 25 provided in the element holding body 14 as illustrated in FIG. 12.

As illustrated in FIG. 12, the coaxial cable 41 which is inserted into and passed through the inside of the shaft 12 passes through the inside of a flexible member 13 to enter the inside of the element holding body 14. As illustrated in FIG. 14, in the coaxial cable 41, the external conductor 41C is exposed from the external coating material 41D in an end portion on the proximal side in the element holding body 14 and further the internal conductor 41A is exposed from the exposed external conductor 41C. The exposed internal conductor 41A is inserted into and passed through the inside of a through-hole 24 of a core material 23, and the distal end thereof is projected from the distal end of the core material 23. The distal end of the internal conductor 41A is electrically connected to one end of the measurement element 22. The distal end of the external conductor 41C positioned on the proximal side of the core material 23 is electrically connected to the other end of the measurement element 22.

As illustrated in FIG. 12, a guide body 55 is provided at an end portion on the distal side of the element holding body 14. The guide body 55 is provided with one sealing member 51 in place of the sealing member 18 and the distal core material 17 of the guide body 15 in the first embodiment. The other configurations of the guide body 55 are the same as those of the guide body 15 of the first embodiment described above. The guide body 55 has a coiled spring 16 supported at the distal end of the element holding body 14 and a distal tip 19 supported at the distal end of the coiled spring 16.

The sealing member 51 has a sealing body portion 52 of a columnar shape fitted into an end portion on the distal side of the element holding body 14. An end portion on the distal side of the sealing body portion 52 has a tapered shape in which the outer diameter decreases toward the distal side and an axial portion 53 of a columnar shape extends from the distal end along the axial center portion of the sealing body portion 52.

The axial portion 53 and the sealing body portion 52 are integrally formed of stainless steel and the sealing body portion 52 is integrally bonded to the element holding body 14. A tip portion of the axial portion 53 is inserted into the axial center portion of the distal tip 19 to be integrally bonded to the distal tip 19. The axial portion 53 prevents the coiled spring 16 from being largely bent by selecting one having high rigidity higher than that of the coiled spring 16.

Also with the blood flow meter 50 of such a configuration according to this embodiment, the mass flow rate changes of the entire blood flow at arbitrary positions of the coronary artery are detectable with high accuracy as with the blood flow meter 10 according to the first embodiment.

Fourth Embodiment

Figure 15:
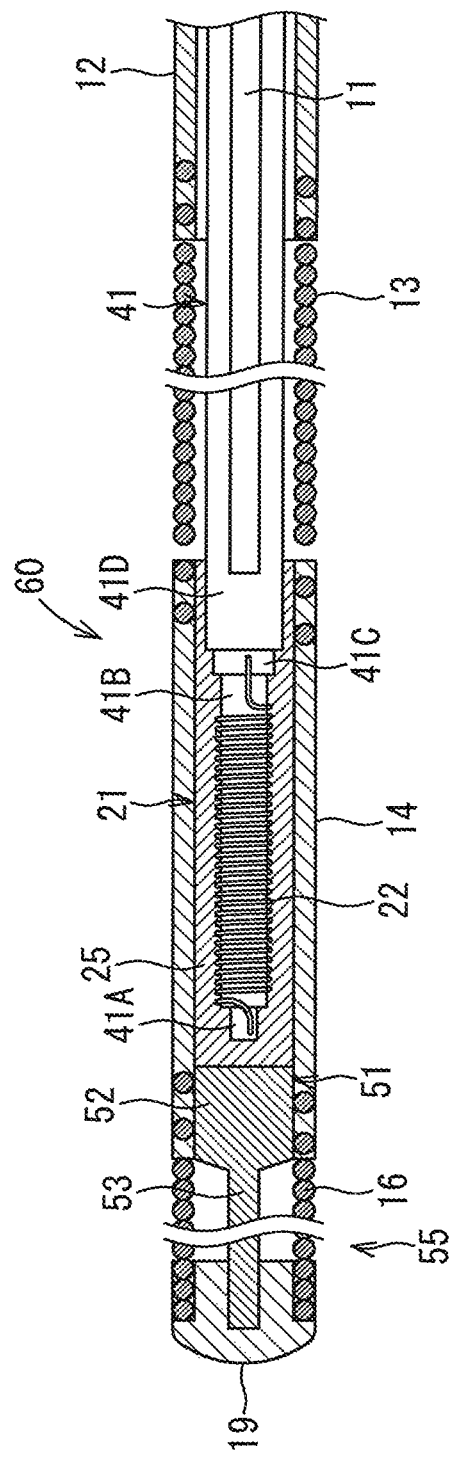
FIG. 15 is a vertical cross-sectional view of a tip portion of a blood flow meter 60 according to a fourth embodiment.

FIG. 15 is a vertical cross-sectional view of a tip portion of a blood flow meter 60 according to a fourth embodiment. Also in the blood flow meter 60, a coaxial cable 41 is inserted into and passed through the inside of a shaft 12 along a core wire 11 as with the third embodiment. The coaxial cable 41 has the same configuration as that of the coaxial cable 41 of the third embodiment.

The blood flow meter 60 according to this embodiment has the same configurations as those of the blood flow meter 50 according to the third embodiment, except the fact that the configuration of an end portion on the distal side of the coaxial cable 41 and the configuration of a flow rate sensor 21 are different.

As illustrated in FIG. 15, the coaxial cable 41 inserted into and passed through the inside of the shaft 12 passes through the inside of the flexible member 13 to enter the inside of the element holding body 14. In the coaxial cable 41, an external conductor 41C is exposed from an external coating material 41D in an end portion on the proximal side in an element holding body 14. The external conductor 41C is exposed with a relatively short length from the external coating material 41D. An internal coating material 41B is exposed from the distal end of the external conductor 41C. The exposed internal coating material 41B is inserted into and passed through the inside of the element holding body 14, and the distal end thereof is positioned near the distal end in the element holding body 14. An internal conductor 41A is exposed with a relatively short length from the distal end of the internal coating material 41B.

Figure 16:
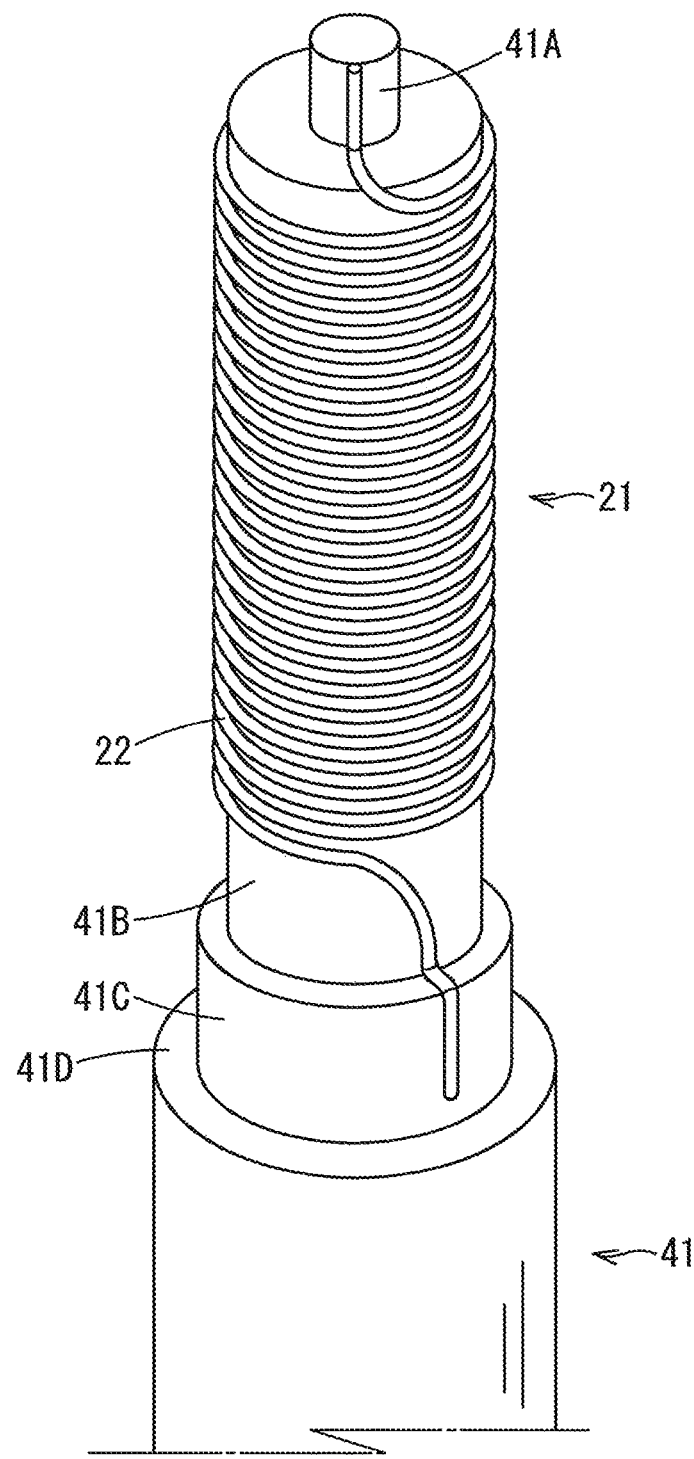
FIG. 16 is a perspective view of a flow rate sensor 21 provided in the blood flow meter 60.

FIG. 16 is a perspective view of a flow rate sensor 21 provided in the element holding body 14. As illustrated in FIG. 16, in the measurement element 22 of the flow rate sensor 21, a nickel wire is spirally wound to be formed into a coil shape on the outer peripheral surface of the internal coating material 41B which is inserted into and passed through the inside of the element holding body 14.

The measurement element 22 is pasted to the outer peripheral surface of the internal coating material 41B with an instant adhesive, for example, so that adjacent nickel wires are separated so as not to be in contact with each other on the outer peripheral surface of the internal coating material 41B. The flow rate sensor 21 is fixed in the element holding body 14 by an insulating member 25 provided in the element holding body 14 as illustrated in FIG. 12.

The internal conductor 41A exposed from the distal end of the internal coating material 41B is electrically connected to one end of the measurement element 22. The external conductor 41C exposed in an end portion on the proximal side of the element holding body 14 is electrically connected to the other end of the measurement element 22.

The internal conductor 41A is fixed in the element holding body 14 by the insulating member 25 provided in the element holding body 14 with the measurement element 22 provided on the outer peripheral surface.

Also with the blood flow meter 60 of such a configuration according to the fourth embodiment, the mass flow rate changes of the blood flow at arbitrary positions of the coronary artery is detectable with high accuracy as with the blood flow meter 50 according to the third embodiment.

The measurement element 22 is provided on the outer peripheral surface of the external coating material of the coaxial cable 41, and therefore a special member for holding the measurement element 22 in the coil shape is not required.

Fifth Embodiment

A blood flow meter according to a fifth embodiment is configured so that a coaxial cable 41 is inserted into and passed through the inside a shaft 12 along a core wire 11 as with the blood flow meter 60 of the fourth embodiment but the configuration of an end portion on the distal side of the coaxial cable 41 is different from that of the fourth embodiment. The configurations other than the configuration of the end portion on the distal side of the coaxial cable 41 are the same as those of the blood flow meter 60 according to the fourth embodiment.

Figure 17:
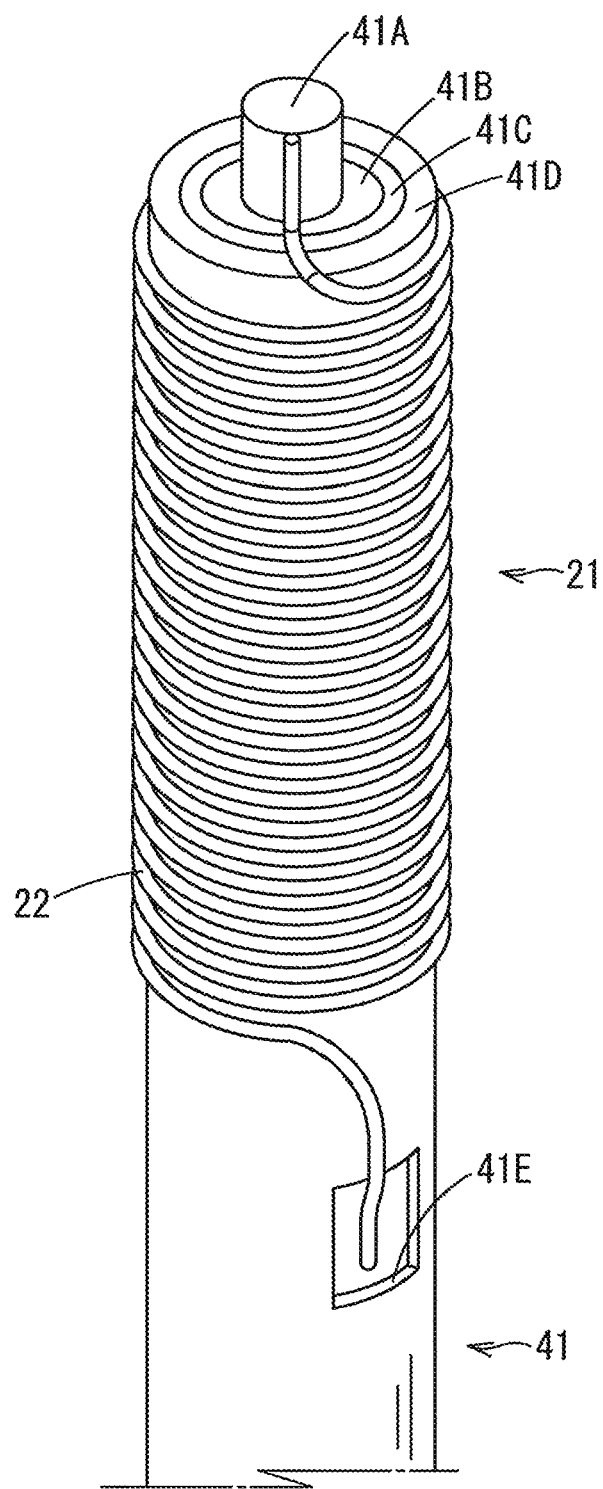
FIG. 17 is a perspective view of a flow rate sensor 21 provided in a blood flow meter 70 according to a fifth embodiment.

FIG. 17 is a perspective view of a flow rate sensor 21 in the blood flow meter according to the fifth embodiment. The coaxial cable 41 inserted into and passed through the inside of the shaft 12 passes through the inside of a flexible member 13 to enter the inside of an element holding body 14, so that the distal end thereof is positioned near a sealing member 51 provided at the distal end of the element holding body 14. At the distal end of the coaxial cable 41, an internal conductor 41A is exposed with a relatively short length from an internal coating material 41B, an external conductor 41C, and an external coating material 41D.

In a measurement element 22 of the flow rate sensor 21, a nickel wire is spirally wound to be formed into a coil shape on the outer peripheral surface of the external coating material 41D which is inserted into and passed through the inside of the element holding body 14. The measurement element 22 is pasted to the outer peripheral surface of the external coating material 41D with an instant adhesive, for example.

The internal conductor 41A exposed at the distal end of the coaxial cable 41 is electrically connected to one end of the measurement element 22. In the coaxial cable 41, an opening portion 41E is formed by removing a part of the external coating material 41D in an end portion on the proximal side of the element holding body 14 and the external conductor 41C is exposed from the opening portion 41E. The external conductor 41C exposed from the opening portion 41E is electrically connected to the other end of the measurement element 22.

The measurement element 22 provided on the outer peripheral surface of the internal conductor 41A is fixed in the element holding body 14 by an insulating member 25 provided in the element holding body 14.

Also with the blood flow meter of such a configuration according to the fifth embodiment, the mass flow rate changes of the blood flow in the arbitrary positions of the coronary artery are detectable with high accuracy as with the blood flow meter 60 according to the fourth embodiment.

Since the measurement element 22 is provided on the outer peripheral surface of the internal coating material exposed from the coaxial cable 41, a special member for holding the measurement element 22 in the coil shape is not required.

[Modification 1]

The measurement element 22 of the flow rate sensor 21 is not limited to the embodiments described above and may be configured so that the measurement element 22 containing the heating resistor can detect the temperature changes on the wall surface of the element holding body 14 over the entire circumference.

For example, a metal wire (wire rod) which is a heating resistor having the temperature-resistance characteristic other than the nickel wire may be used as the measurement element 22. As the metal wire, a platinum wire in which the product ($\rho \cdot \alpha$) of the electric resistivity $\rho$ and the temperature coefficient $\alpha$ is 0.042 ($\mu\Omega \cdot cm/°$ C.) is preferably used.

Moreover, in the measurement element 22 of the flow rate sensor 21, a nickel wire or the like as the heating resistor may be formed into a predetermined shape by electroforming. Furthermore, the measurement element 22 may contain a resistance heating element formed into a predetermined shape by a MEMS (Micro Electro Mechanical Systems).

[Modification 2]

Each of the embodiments described above may be configured so that a temperature sensor, such as a thermocouple, which detects the temperature of the blood flow is provided in the flexible member 13. The temperature sensor is disposed so as to be in contact with the blood flow flowing into the flexible member 13. An output of the temperature sensor is given to the calculation portion 32 of the calculation control portion 30 with the leads inserted into and passed through the inside of the shaft 12. The calculation portion 32 is configured so as to compensate voltage changes of the measurement element 22 in the flow rate sensor 21 based on the temperature of the blood flow detected by the temperature sensor. Thus, even when the temperature of the blood flow changes, the mass flow rate changes in the blood flow are measurable with higher accuracy.

[Modification 3]

The embodiments described above are configured so as to supply a fixed direct current to the measurement element 22 in the flow rate sensor 21 but a configuration of supplying an alternating current to the measurement element 22 may be acceptable. In a catheter for heating an organ of a living body, a 100 kHz alternating current is considered to be safe. Therefore, when an alternating current is supplied to the measurement element 22, the alternating current is preferably set to 100 kHz.

[Modification 4]

In the embodiments described above, the calculation portion 32 is configured so as to calculate the flow velocity of the blood flow based on the electrical resistance value changes of the measurement element 22 but the present invention is not limited to such a configuration. For example, a configuration may be acceptable in which a measurement unit for measuring the intravascular lumen area by ultrasonic waves or the like is provided in the blood flow meter 10, and then the mass flow rate (g/s) of the blood flow may be calculated based on the intravascular lumen area obtained by the measurement unit and the mass flow rate per unit area (g/mm$^2$·S) of the blood flow obtained by the flow rate sensor 21 according to the following expression, Mass flow rate (g/s)=[Mass flow rate per unit time passing per unit area (g/mm$^2$·s)]×[Intravascular Lumen Area (mm$^2$)]

Moreover, a configuration may be acceptable in which the volume flow rate of the blood flow is determined by the calculation portion 32. In this case, the volume flow rate is calculated by multiplying the mass flow rate per unit area of the blood flow obtained by the flow rate sensor 21 (g/mm$^2$·s) by the reciprocal of the blood density (g/ml).

REFERENCE SIGNS LIST

10 Blood flow meter
11 Core wire
12 Shaft
13 Flexible member
14 Element holding body
15 Guide body
16 Coiled spring
17 Distal core material
20 Measurement device
21 Flow rate sensor
22 Measurement element
23 Core material
24 Through-hole
25 Insulating member
26 First lead
26A Copper wire
26B Insulation coating material
27 Second lead
27A Copper wire
27B Insulation coating material
30 Calculation control portion
31 Power supply portion
32 Calculation portion
40 Blood flow meter
41 Coaxial cable
41A Internal conductor
41B Internal coating material
41C External conductor
41D External coating material
41E Opening portion
50 Blood flow meter
60 Blood flow meter

The invention claimed is:

1. A blood flow meter slidable through a catheter tube, the blood flow meter comprising:
a hollow shaft which has flexibility and is insertable into a blood vessel, the hollow shaft being distinct from the catheter tube;
an element holding body which is provided at a distal side of the hollow shaft so as to be coaxial with the hollow shaft and which has a tubular shape and an outer diameter smaller than or equal to an outer diameter of the hollow shaft;
a first core wire, a first lead wire, and a second lead wire extending through the hollow shaft, the first core wire extending to a vicinity of the element holding body, the first lead wire and the second lead wire extending into a proximal end of the element holding body, the first core wire being solid and having a bending rigidity higher than the hollow shaft;
a thermal conductive insulating member located concentrically within the element holding body so as to be radially inward of an inner diameter of said element holding body;
a flow rate sensor comprising an axially-extending, electrically-insulative core and a metal wire wrapped around the axially-extending, electrically-insulative core into a coil shape, the metal wire serving as a measurement element of the flow rate sensor by having a temperature-resistance characteristic, all of the measurement element being located concentrically within the element holding body with a first portion of the thermal conductive insulating member being located between the measurement element and an inner wall of said element holding body; and
wherein the first lead wire passes through the axially-extending, electrically-insulative core and terminates at a distal end of the flow rate sensor, the first lead wire being electrically coupled to a distal end of the measurement element, the second lead wire being electrically coupled to a proximal end of the measurement element;
wherein a distal portion of the thermal conductive insulating member covers an entirety of an axial end face of the axially-extending, electrically-insulative core; and
wherein for a first cross section of the blood flow meter, along a circumferential portion of said first cross section are located in a radially inward direction transverse to an axial direction along which the element holding body extends: the inner wall of the element holding body, said first portion of said thermal conductive insulating member, a corresponding portion of the measurement element, and then the axially-extending, electrically-insulative core, so that the measurement element detects temperature changes of the inner wall of the element holding body over a circumference of the element holding body.

2. The blood flow meter according to claim 1, wherein the metal wire is a nickel wire or a platinum wire.

3. The blood flow meter according to claim 1, wherein an outer diameter of the hollow shaft is $0.36$ mm or less.

4. The blood flow meter according to claim 1, wherein the insulating member is a resin having thermal diffusivity of 0.06 to 0.21 mm2/s.

5. The blood flow meter according to claim 1, wherein a flexible member of a cylindrical shape having flexibility is provided at a distal end of the hollow shaft so as to be coaxial with the hollow shaft, and
the element holding body is provided at a distal end of the flexible member so as to be coaxial with the flexible member.

6. The blood flow meter according to claim 1, wherein a guide body of a cylindrical shape having flexibility is provided at a distal end of the element holding body so as to be coaxial with the element holding body,
the guide body comprising:
a coiled spring made of a radiopaque metal wire; and
a second core wire having a bending rigidity higher than the coiled spring, the second core wire originating distal to the measurement element; and
wherein the second core wire is separate from and distal to both of the flow rate sensor's core and a distal end of the first lead wire.

7. The blood flow meter according to claim 1, as part of a measurement device configured to calculate a velocity of blood flow based on electrical resistance value changes of the measurement element as determined from an electrical signal passing through said measurement element.

8. The blood flow meter of claim 1, wherein the element holding body comprises an opening formed in a peripheral wall of the element holding body exposing a third portion of the thermal conductive insulating member.

9. The blood flow meter of claim 1, wherein the metal wire is a bare, unsheathed metal wire wrapped around the axially-extending, electrically-insulative core into a coil shape having adjacent loops that are spaced apart, and
wherein the thermal conductive insulating member includes second portions respectively securing an insulation state between adjacent loops of the bare, unsheathed metal wire on the outer peripheral surface of the core.

10. A blood flow meter comprising:
a hollow shaft which has flexibility and is insertable into a blood vessel;
an element holding body which is provided on a distal side of the hollow shaft so as to be coaxial with the hollow shaft and which has a tubular shape and an outer diameter smaller than or equal to an outer diameter of the hollow shaft;
a thermal conductive insulating member located concentrically within the element holding body so as to be radially inward of an inner diameter of said element holding body;
a flow rate sensor which has a measurement element comprising a metal wire having a temperature-resistance characteristic, all of the measurement element being located concentrically within the element holding body; and
a coaxial cable supplying electric power to the measurement element,
wherein the metal wire is provided on an outer peripheral surface of an external coating material of the coaxial cable or an internal coating material exposed from the coaxial cable;
wherein the metal wire is wrapped into a coil shape, all of the measurement element being located concentrically within the element holding body with a first portion of the thermal conductive insulating member being located between the measurement element and an inner wall of the element holding body; and
wherein the thermal conductive insulating member covers an entirety of an axial end face of the coaxial cable; and
wherein for a first cross section of the blood flow meter, along a circumferential portion of said first cross section are located in a radially inward direction transverse to an axial direction along which the element holding body extends: the inner wall of the element holding body, said first portion of said thermal conductive insulating member, a corresponding portion of the measurement element, and then the coaxial cable, so that the measurement element detects temperature changes of the inner wall of the element holding body over a circumference of the element holding body.

11. The blood flow meter according to claim 10, wherein the metal wire is a bare, unsheathed metal wire wrapped into a coil shape having adjacent loops that are spaced apart; and
   wherein the thermal conductive insulating member includes second portions respectively securing an insulation state between adjacent loops of the bare, unsheathed metal wire.

12. The blood flow meter according to claim 10, wherein a distal portion of the thermal conductive insulating member covers an entirety of a distal end of the flow rate sensor and a distal end of the first lead wire so that a cross section of the element holding body distal to the flow rate sensor consists only of said distal portion of the thermal conductive insulating member.

13. The blood flow meter according to claim 10, wherein the blood flow meter is slidable through a catheter tube and said hollow shaft is distinct from the catheter tube; and further comprising:
   a core wire extending through the hollow shaft with the coaxial cable, the core wire being solid so that the coaxial cable extends alongside the core wire, the core wire having a bending rigidity higher than the hollow shaft; and
   wherein a first conductor of the coaxial cable is coupled to one end of the metal wire and a second conductor of the coaxial cable is coupled to an opposite end of the metal wire.

14. The blood flow meter according to claim 10, wherein a distal portion of the thermal conductive insulating member covers said entirety of said axial end face of the coaxial cable so that a cross section of the element holding body distal to the flow rate sensor consists only of said distal portion of the thermal conductive insulating member.

15. A blood flow meter slidable through a catheter tube, the blood flow meter comprising:
   a hollow shaft which has flexibility and is insertable into a blood vessel, the hollow shaft being distinct from the catheter tube;
   a first core wire which is solid and has a bending rigidity higher than the shaft;
   a first lead wire and a second lead wire extending through the shaft alongside the first core wire,
   an element holding body which is provided at a distal side of the shaft so as to be coaxial with the shaft and which has a tubular shape and an outer diameter smaller than or equal to an outer diameter of the shaft;
   a thermal conductive insulating member located concentrically within the element holding body so as to be radially inward of an inner diameter of said element holding body;
   a flow rate sensor comprising an axially-extending, electrically-insulative core and a metal wire wrapped around the core into a coil shape;
   wherein the axially-extending, electrically-insulative core is distinct from the first core wire and has an axially-extending through-channel;
   wherein the metal wire serves as a measurement element of the flow rate sensor by having a temperature-resistance characteristic, all of the measurement element being located concentrically within the element holding body with a first portion of the thermal conductive insulating member being located between the measurement element and an inner wall of said element holding body;
   wherein the first lead wire and second lead wire extend into a proximal end of the element holding body, the first lead wire passing through the through-channel of the axially-extending, electrically-insulative core and being electrically coupled to a distal end of the measurement element, the second lead wire being electrically coupled to a proximal end of the measurement element;
   wherein a distal portion of the thermal conductive insulating member covers an entirety of an axial end face of the axially-extending, electrically-insulative core; and
   wherein for a first cross section of the blood flow meter, along a circumferential portion of said first cross section are located in a radially inward direction transverse to an axial direction along which the element holding body extends: the inner wall of the element holding body, said first portion of said thermal conductive insulating member, a corresponding portion of the measurement element, and then the axially-extending, electrically-insulative core, so that the measurement element detects temperature changes of the inner wall of the element holding body over a circumference of the element holding body.

\* \* \* \* \*

UNITED STATES PATENT AND TRADEMARK OFFICE
CERTIFICATE OF CORRECTION

| | | |
|---|---|---|
| PATENT NO. | : 11,330,990 B2 | Page 1 of 1 |
| APPLICATION NO. | : 15/539901 | |
| DATED | : May 17, 2022 | |
| INVENTOR(S) | : Sano Yoshihiko et al. | |

It is certified that error appears in the above-identified patent and that said Letters Patent is hereby corrected as shown below:

On the Title Page

At item (73) Assignees, please cancel the text "; Harada Electronic Industry Ltd."

Signed and Sealed this
Twenty-sixth Day of September, 2023

Katherine Kelly Vidal
*Director of the United States Patent and Trademark Office*